(12) United States Patent
Stahler et al.

(10) Patent No.: US 8,108,069 B2
(45) Date of Patent: Jan. 31, 2012

(54) ROBOTIC CATHETER SYSTEM AND METHODS

(75) Inventors: Gregory J. Stahler, San Jose, CA (US); Frederic H. Moll, Woodside, CA (US)

(73) Assignee: Hansen Medical, Inc., Mountain View, CA (US)

( * ) Notice: Subject to any disclaimer, the term of this patent is extended or adjusted under 35 U.S.C. 154(b) by 987 days.

(21) Appl. No.: 11/972,581

(22) Filed: Jan. 10, 2008

(65) Prior Publication Data
US 2008/0167750 A1 Jul. 10, 2008

Related U.S. Application Data

(60) Provisional application No. 60/879,911, filed on Jan. 10, 2007.

(51) Int. Cl.
*G06F 19/00* (2011.01)

(52) U.S. Cl. .......... 700/245; 700/83; 700/246; 700/248; 700/262

(58) Field of Classification Search .................. 700/245, 700/83, 246, 248, 249, 262; 600/1, 109, 600/407
See application file for complete search history.

(56) References Cited

U.S. PATENT DOCUMENTS

| | | | | |
|---|---|---|---|---|
| 5,441,505 A * | 8/1995 | Nakamura | | 606/130 |
| 5,807,377 A | 9/1998 | Madhani et al. | | |
| 5,845,540 A * | 12/1998 | Rosheim | | 74/490.05 |
| 5,855,583 A * | 1/1999 | Wang et al. | | 606/139 |
| 5,876,325 A * | 3/1999 | Mizuno et al. | | 600/102 |
| 6,301,526 B1 | 10/2001 | Kim et al. | | |
| 6,364,888 B1 | 4/2002 | Niemeyer et al. | | |
| 2003/0208187 A1 * | 11/2003 | Layer | | 606/1 |
| 2004/0176751 A1 | 9/2004 | Weitzner et al. | | |
| 2005/0137478 A1 * | 6/2005 | Younge et al. | | 600/437 |
| 2005/0197530 A1 * | 9/2005 | Wallace et al. | | 600/116 |
| 2005/0222554 A1 * | 10/2005 | Wallace et al. | | 606/1 |
| 2006/0084945 A1 | 4/2006 | Moll et al. | | |
| 2006/0095022 A1 * | 5/2006 | Moll et al. | | 606/1 |
| 2006/0100610 A1 * | 5/2006 | Wallace et al. | | 606/1 |

(Continued)

FOREIGN PATENT DOCUMENTS
EP 1681029 7/2006
(Continued)

OTHER PUBLICATIONS

PCT International Search Report for PCT/US2008/050797, Applicant Hansen Medical Inc., Forms PCT/ISA/210 and 220, dated Jun. 25, 2008 (6 pages).

(Continued)

*Primary Examiner* — Khoi Tran
*Assistant Examiner* — Jorge Peche
(74) *Attorney, Agent, or Firm* — Vista IP Law Group LLP

(57) ABSTRACT

A robotic instrument system and method, comprising at least two instrument drive assemblies each detachably coupled to a respective instrument assembly. Each instrument assembly comprising an elongate, flexible guide instrument configured to be inserted into a patient's body. The instrument drive assemblies comprise one or more motors configure to operate a respective instrument assembly. One or more controllers are operatively coupled to the instrument drive assemblies. The method comprises maneuvering a distal end of each of the respective guide instruments into a patient's heart by actuating the respective drive assembly performing a procedure controlled by the one or more controllers.

14 Claims, 51 Drawing Sheets

U.S. PATENT DOCUMENTS

| | | | |
|---|---|---|---|
| 2006/0111692 A1* | 5/2006 | Hlavka et al. | 604/890.1 |
| 2006/0200026 A1 | 9/2006 | Wallace et al. | |
| 2006/0253108 A1 | 11/2006 | Yu et al. | |
| 2006/0276775 A1 | 12/2006 | Rosenberg et al. | |
| 2006/0293643 A1* | 12/2006 | Wallace et al. | 606/1 |
| 2007/0043338 A1 | 2/2007 | Moll et al. | |
| 2007/0043349 A1* | 2/2007 | Swanson et al. | 606/41 |
| 2007/0156123 A1 | 7/2007 | Moll et al. | |
| 2007/0197896 A1 | 8/2007 | Moll et al. | |
| 2007/0203507 A1* | 8/2007 | McLaughlin et al. | 606/144 |
| 2008/0009747 A1* | 1/2008 | Saadat et al. | 600/471 |

FOREIGN PATENT DOCUMENTS

| | | |
|---|---|---|
| WO | 9501757 | 1/1995 |

OTHER PUBLICATIONS

PCT Written Opinion of the International Search Authority for PCT/US2008/050797, Applicant Hansen Medical, Inc., Form PCT/ISA/237 dated Jun. 25, 2008 (8 pages).

* cited by examiner

ROBOTIC CATHETER SYSTEM AND METHODS

RELATED APPLICATION DATA

The present application claims the benefit under 35 U.S.C. §119 to U.S. Provisional Patent Application Ser. No. 60/879, 911, filed on Jan. 10, 2007. The foregoing application is hereby incorporated by reference into the present application in its entirety.

FIELD OF INVENTION

The invention relates generally to robotically controlled systems, such as telerobotic surgical systems, and more particularly to a robotic catheter system for performing minimally invasive diagnostic and therapeutic procedures.

BACKGROUND

Robotic interventional systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be accessed via naturally-occurring pathways such as blood vessels, other lumens, via surgically-created wounds of minimized size, or combinations thereof.

SUMMARY OF THE INVENTION

In one embodiment, the present invention is directed to a robotic catheter system comprising at least two instrument drive assemblies each removably coupled to a respective instrument assembly. Each instrument assembly comprises an elongate, flexible instrument configured to be inserted into a patient's body, for example, an intravascular catheter. The instrument drive assemblies may comprises drive elements configured to control the respective instrument assemblies and instruments. One or more controllers are operatively coupled to the instrument drive assemblies and comprise a user interface that is operated by a user to operate the instrument drive assemblies. For example, each instrument drive assembly may be operatively coupled to a separate controller, and the separate controllers may be in operative communication with each other. Alternatively, a single controller may be configured to control multiple instrument drive assembly, in which case multiple instrument drive assemblies may be operatively coupled to a single controller. The controllers may further comprise one or more displays with the controller configured to display images of a surgical site, and/or the instrument assemblies.

In another aspect of the present invention, the instrument drive assemblies are coupled to separate support assemblies. The support assemblies are adapted to support the drive assemblies. The support assemblies may be configured to attach to an operating table or other operating room structure, or the support structures may be stand alone modules such as a cart or a stand. The support assembly comprises a plurality of rigid links coupled by braked joints, such as electronically braked joints or manually braked joints. The joints prevent motion of the links when the brake is applied, but allow motion of the links when the brake is released. Alternatively, the links and joints of the support assembly may be articulating robotic arms which are controllable by a controller, such as the master controller.

In another embodiment of the present invention, two or more instrument drive assemblies may be coupled to the same support assembly. The instrument drive assemblies may be coupled to the support assembly with an articulating coupling which allows the position (such as orientation and/or location) of the instrument drive assemblies to be adjusted.

In still another embodiment of the present invention, two or more drive assemblies may be coupled to a mounting assembly and the mounting assembly is coupled to the support assembly. The mounting assembly may be rotatably coupled to the support assembly to allow positional adjustment of the drive assemblies.

In another embodiment of the present invention, a method for performing a minimally invasive intracardiac surgical procedure utilizes a robotic catheter system. The robotic catheter system comprises a first instrument drive assembly configured to operate a first instrument assembly. The first instrument assembly is coupled to the first instrument drive assembly, and comprises an elongate, flexible first instrument having a distal end. A second instrument drive assembly, same or similar to the first instrument drive assembly, is coupled to a second instrument assembly, same or similar to the first instrument assembly. Various surgical instruments, such as imaging devices, cutting tools, ablation tools, etc. may be provided on the distal end of the first and second instruments. The distal end of the first instrument is inserted into a patient's body and is maneuvered into the patient's heart by actuating the first instrument drive assembly. The distal end of the second instrument is also inserted into the patient's body and is maneuvered into the patient's heart by actuating the second instrument drive assembly. The distal ends of the first and second instruments may be maneuvered into the heart, for example, both through the inferior vena cava, both through the superior vena cava, or one through the inferior vena cava and the other through the superior vena cava, or through other vascular lumens which enter the heart. With the first and second instruments located within the heart, various intracardiac surgical procedures may be performed, such as a patent foramen ovale (PFO), a transseptal mitral annulus, heart tissue ablation for treating arrhythmia, or other suitable heart procedures.

BRIEF DESCRIPTION OF THE DRAWINGS

The drawings illustrate the design and utility of illustrated embodiments of the invention, in which similar elements are referred to by common reference numerals. In addition, elements having the same reference numeral but different letter identifiers [e.g. a robotic catheter assemblies (12a and 12b)], are the same or substantially similar elements, and may be described commonly without the letter identifier [e.g. robotic catheter (12)].

DETAILED DESCRIPTION OF THE ILLUSTRATED EMBODIMENTS

Figure 1A:
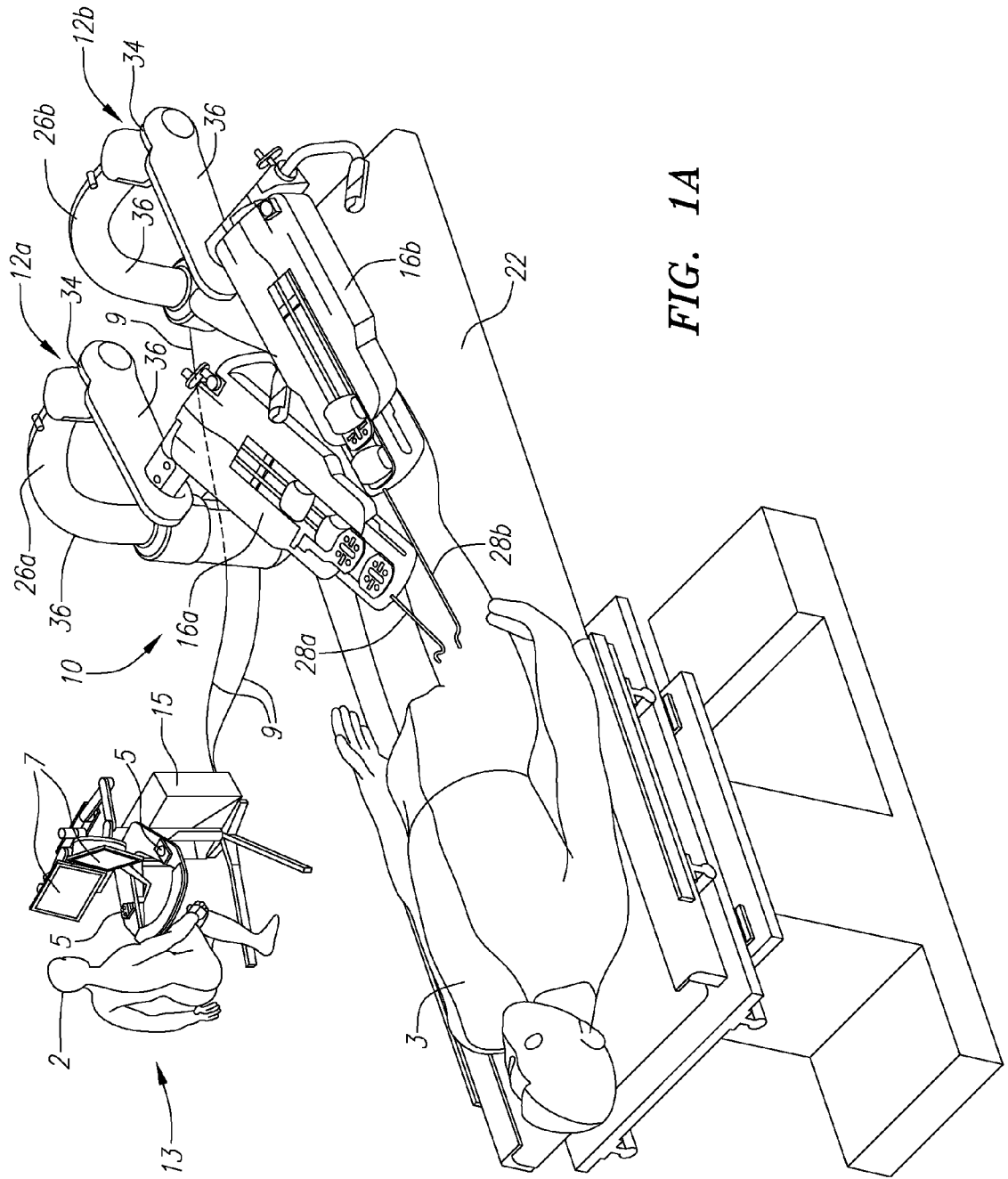
FIG. 1A illustrates one embodiment of a robotic catheter system in accordance with the present invention.

Referring to FIG. 1A, one embodiment of a robotic catheter system (10) is depicted in relation to an operating table (22) and a patient (3) lying on the table. The system (10) of FIG. 1A comprises two robotic catheter assemblies (12a and 12b). The first robotic catheter assembly (12a) comprises a support assembly (26a) operatively coupled to an instrument drive assembly (16a) (also referred to as an "instrument driver"). An instrument assembly (28a) is detachably coupled to the instrument driver (16a). Similarly, the second robotic catheter assembly (12b) comprises a support assembly (26b) operatively coupled to an instrument driver (16b), and an instrument assembly (28b) is detachably coupled to the instrument driver (16a).

The robotic catheter system (10) further comprises one or more controllers (15) operatively coupled to the instrument drive assemblies (16a and 16b). The controllers (15) may be a part of an operator control station (13) located remotely from the operating table (22) and adjacent to an operator (2). The operator control station (13) comprises various input devices (5), and display devices (7), all operatively coupled to the controller (13), as is known in the art.

Figure 1B:
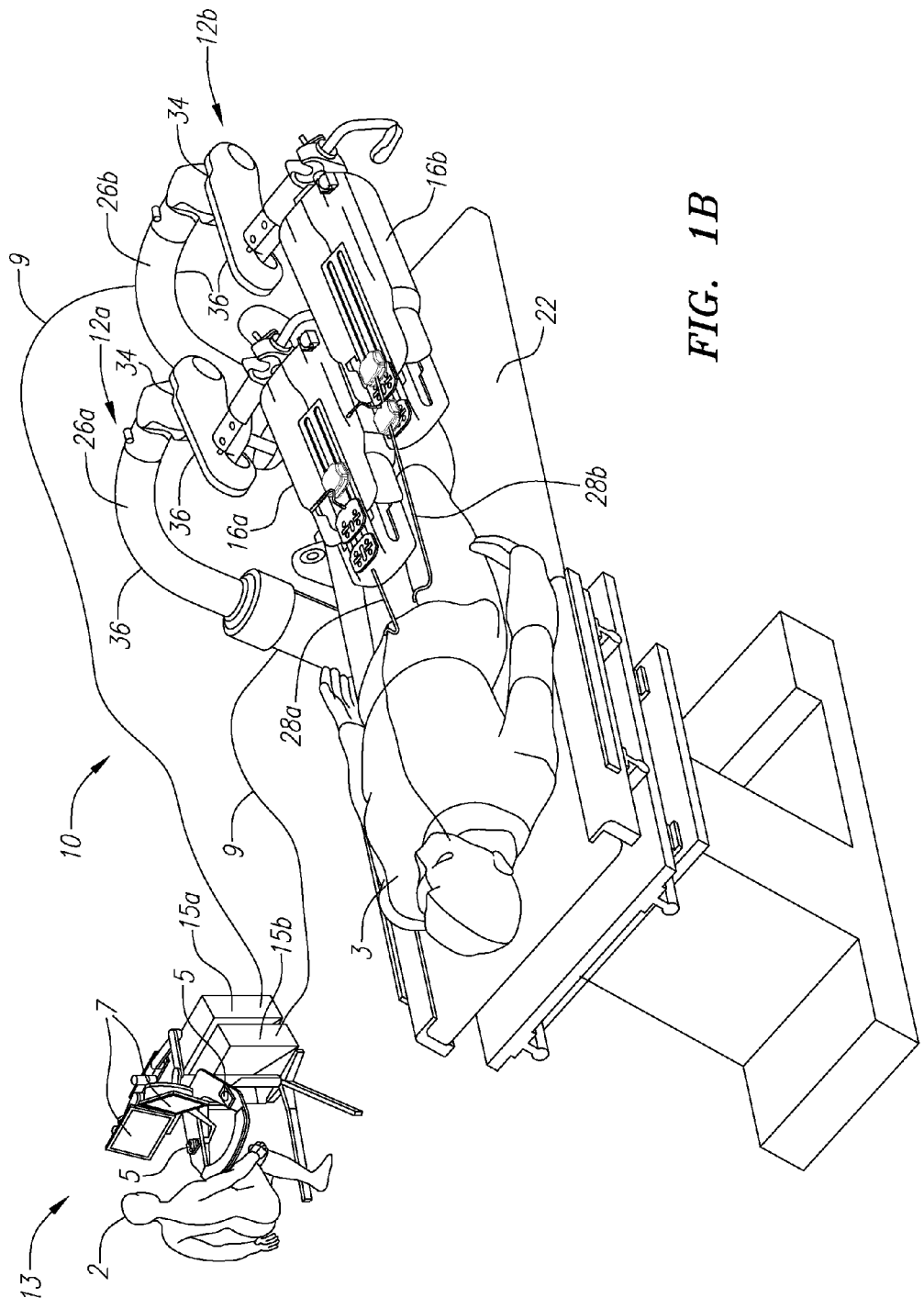
FIG. 1B illustrates an embodiment of a robotic catheter system with the system configured to enter opposite femoral arteries.
Figure 2A:
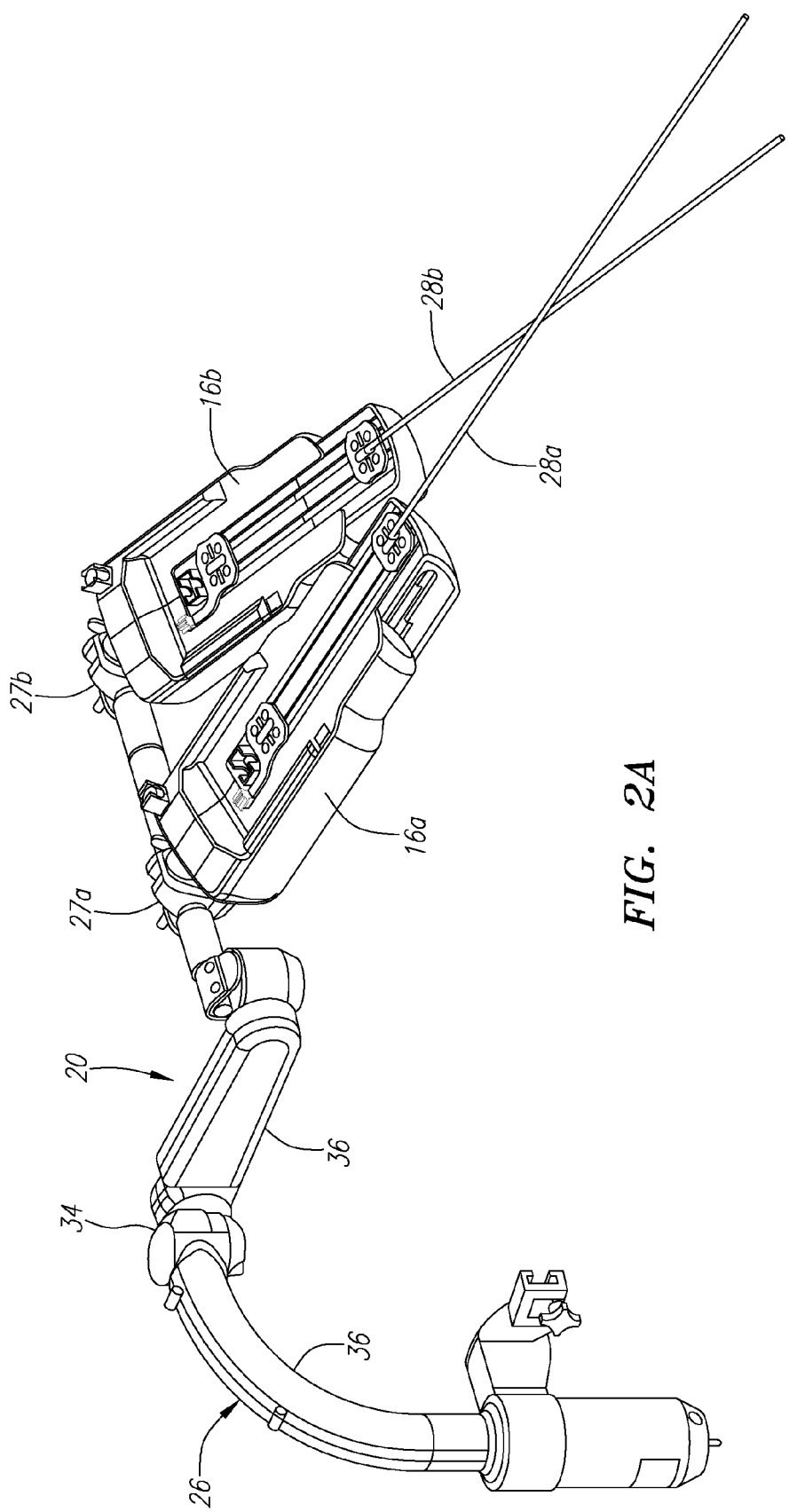
FIGS. 2A-2E illustrate multiple views of another embodiment of a robotic catheter system in accordance with the present invention.
Figure 2B:
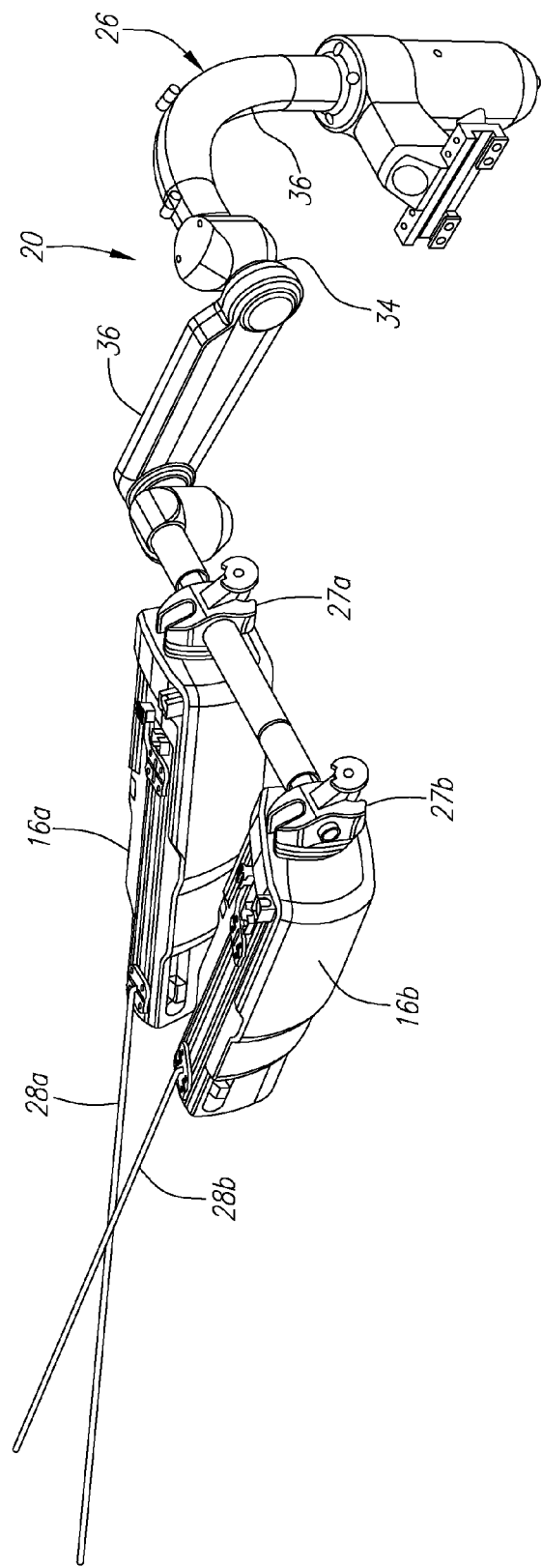
Figure 2C:
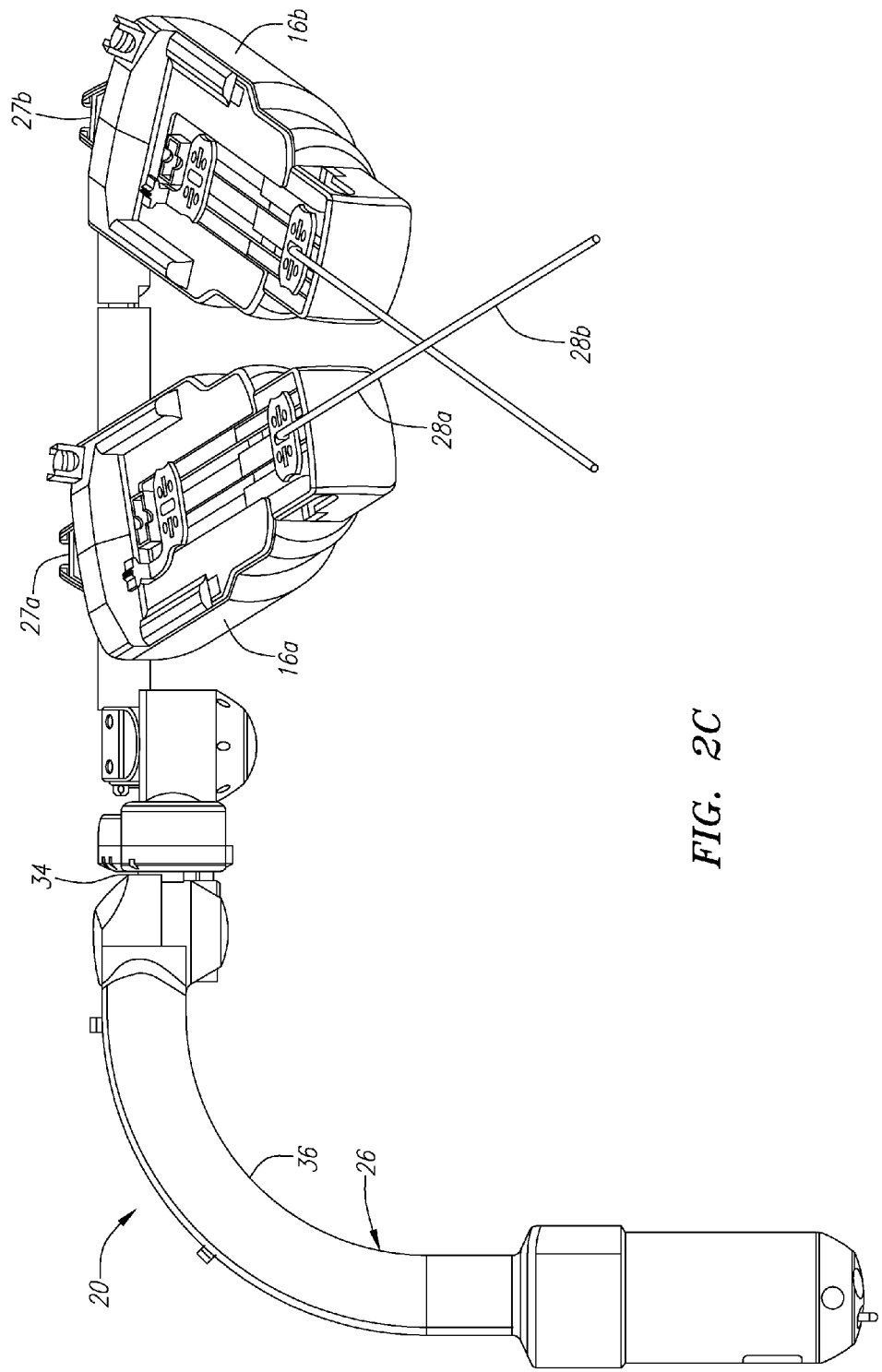
Figure 2D:
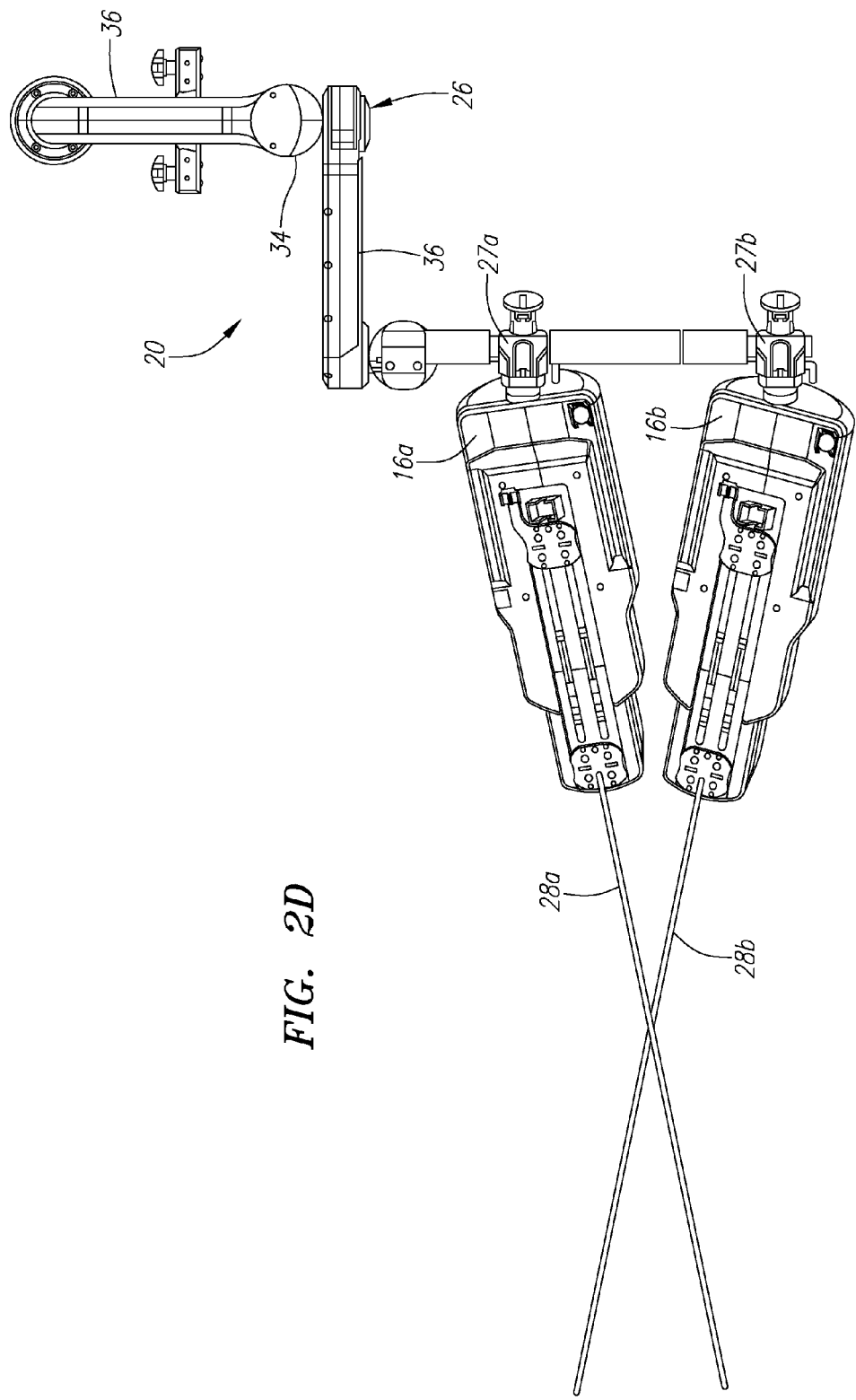
Figure 2E:
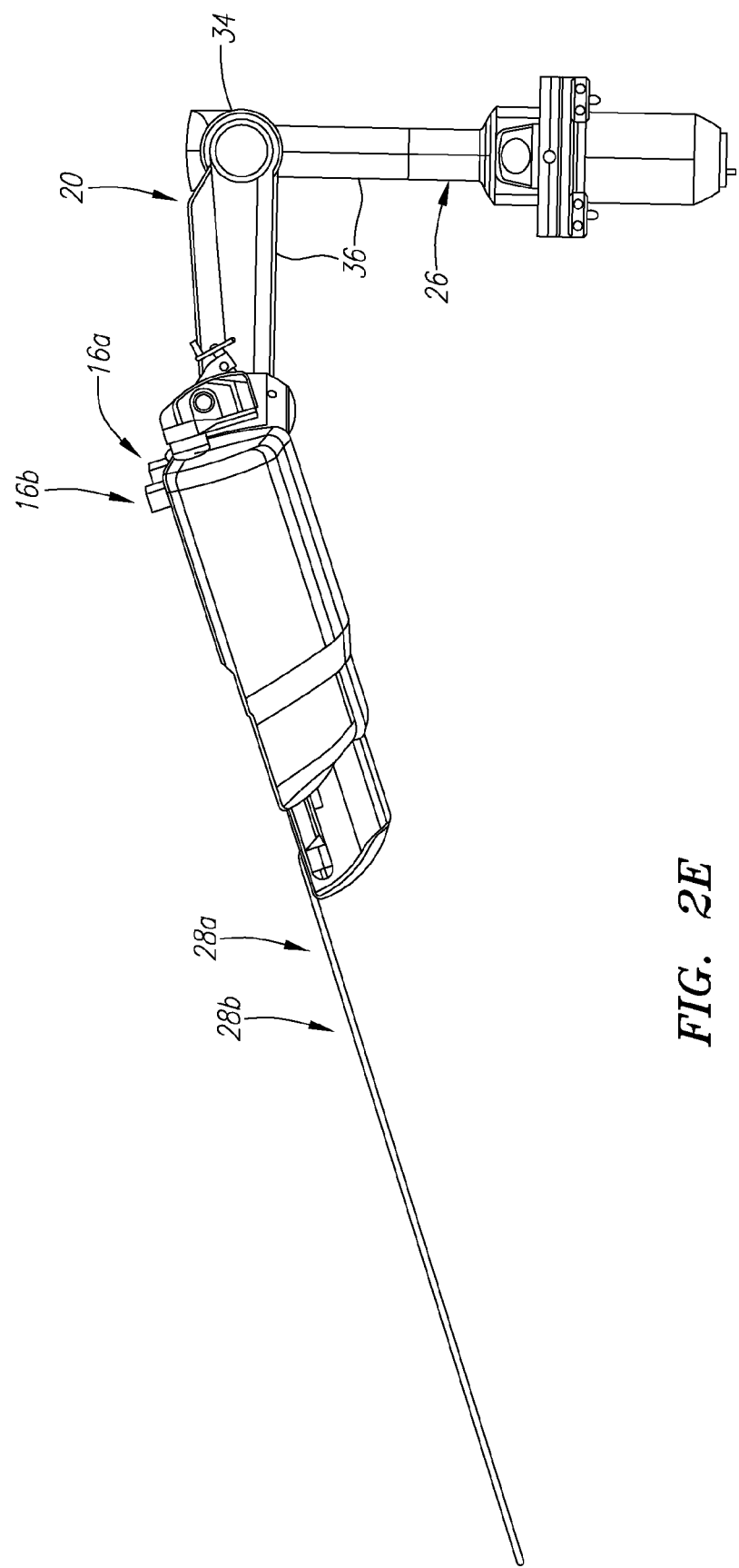

The embodiment of FIG. 1A includes a single controller (15) which is operatively coupled to, and configured to control, both of the instrument drive assemblies (16a and 16b), through a communication link (9) which may connect via the support assemblies (26a and 26b). Alternatively, as shown in FIG. 1B, the instrument drive assemblies (16a and 16b) are operatively coupled to separate controllers (15a and 15b), and the controllers (15a and 15b) are in operative communication through a communication link. The one or more controllers (15) are configured to selectively actuate respective motors in the first and second instrument in the first and second instrument drive assemblies (16a and 16b) to operate the first and second instrument assemblies (28a and 28b). For instance, the one or more controllers (15) may control the movement of the distal end portions of the first and second instrument assemblies (28a and 28b) and/or the actuation of instruments disposed on the distal end of the first and second instrument assemblies (28a and 28b), in response to control signals, generated, at least in part, by the one or more input devices (5).

The instrument assemblies (28) are elongate, flexible devices which are configured to be inserted into a patient's body (3). As non-limiting examples, an instrument assembly 18 may comprise an intravascular catheter, an endoscopic surgical instrument or other medical instrument. The instrument assembly (28) may comprise a robotic guide instrument (18), or a coaxially coupled and independently controllable robotic sheath instrument (30) and a robotic guide instrument (18) (see FIG. 6A, for example) which are configured to be operable via the instrument driver (16) such that the instrument driver can operate to steer the robotic sheath instrument and robotic guide instrument, and also to operate tools and devices (50) which may be provided on the instrument assembly (28) (e.g. an imaging device or cutting tool disposed on the distal end of the instrument assembly (28)). Alternatively, manually steerable and operable instrument assemblies may also be utilized. Thus, all of the technologies described herein may be utilized with manually or robotically steerable instruments, such as those described in the below-referenced patent application, U.S. patent application Ser. No. 11/481,433.

Exemplary embodiments of a control station (13), a robotic catheter assembly (12), and its components including the support assembly (26), the instrument driver (16), the instrument assembly (28), robotic sheath instrument (30), robotic guide instrument (18) and various instruments (50), are described in detail in the following U.S. Patent Applications, and are incorporated herein by reference in their entirety:

U.S. patent application Ser. No. 10/923,660, filed Aug. 20, 2004; U.S. patent application Ser. No. 10/949,032, filed Sep. 24, 2005; U.S. patent application Ser. No. 11/073,363, filed Mar. 4, 2005; U.S. patent application Ser. No. 11/173,812, filed Jul. 1, 2005; U.S. patent application Ser. No. 11/176,954, filed Jul. 6, 2005; U.S. patent application Ser. No. 11/179,007, filed Jul. 6, 2005; U.S. patent application Ser. No. 11/202,925, filed Aug. 12, 2005; U.S. patent application Ser. No. 11/331,576, filed Jan. 13, 2006; U.S. patent application Ser. No. 11/418,398, filed May 3, 2006; U.S. patent application Ser. No. 11/481,433, filed Jul. 3, 2006; U.S. patent application Ser. No. 11/637,951, filed Dec. 11, 2006; U.S. patent application Ser. No. 11/640,099, filed Dec. 14, 2006; and U.S. Provisional Patent Applications Nos. 60/833,624, filed Jul. 26, 2006 and 60/835,592, filed Aug. 3, 2006.

Accordingly, only those features and aspects of those components necessary for an understanding of the present invention will be described in detail herein. As an example, the support assembly (26) comprises a plurality of rigid links (36) which are coupled by joints (34). The rigid links (36) and joints (34) may be positionable by a simple locking of the joints, or they may be robotically controlled. The joints may be electronically braked or manually braked. In one embodiment, the rigid links (36) may be coupled by mechanically lockable joints, which may be locked and unlocked manually using, for example, locking pins, screws, or clamps. The joints allow motion of the links when the brake is released, and prevent motion of the links when the brake is applied. In this way, the support assembly (26) can be adjusted to position instrument driver (16) as desired for the procedure being performed. The support assembly (26) may be configured to attach to the operating table (22), a cart or a stand, or it may be a stand-alone module.

Referring back to FIG. 1A, the depicted instrument assembly (28) comprises a guide instrument (18) that is movably positioned within the working lumen of a sheath instrument (30) to enable relative insertion of the two instruments (30, 18), relative rotation, or "roll" of the two instruments (30, 18), and relative steering or bending of the two instruments (30, 18) relative to each other, particularly when a distal portion of the guide instrument (18) is inserted beyond the distal tip of the sheath instrument (30). As shown in FIG. 1A, the first and second robotic catheter assemblies (12a and 12b) may be positioned and oriented utilizing the first and second support assemblies (26a and 26b) to enter, for example, the same femoral artery, as depicted in FIG. 1A, or opposite femoral arteries, as depicted in FIG. 1B.

Referring to FIGS. 2A-2E, another embodiment of a robotic catheter system 20 is depicted in which first and second first and second instrument drivers (16a and 16b) are both mounted to a single support assembly 26. First and second instrument assemblies (28a depicted behind 28b) coupled to the first and second instrument drivers (16a, 16b0 are also depicted. Such embodiment can facilitate a smaller coupling interface with the operating table (22) than with configurations such as those depicted in FIGS. 1A and 1B, wherein each instrument driver (16a and 16b) is supported by its own setup structure. Each instrument driver (16) is coupled to the support assembly (26) using adjustable couplings (27a and 27b) which allow the position of the instrument drivers (16) to be adjusted. The couplings 27 may allow simple rotational movement, or they may be articulating, such as a gimbal, ball joint or multiple joint, to allow multiple degrees of adjustment.

Figure 3:
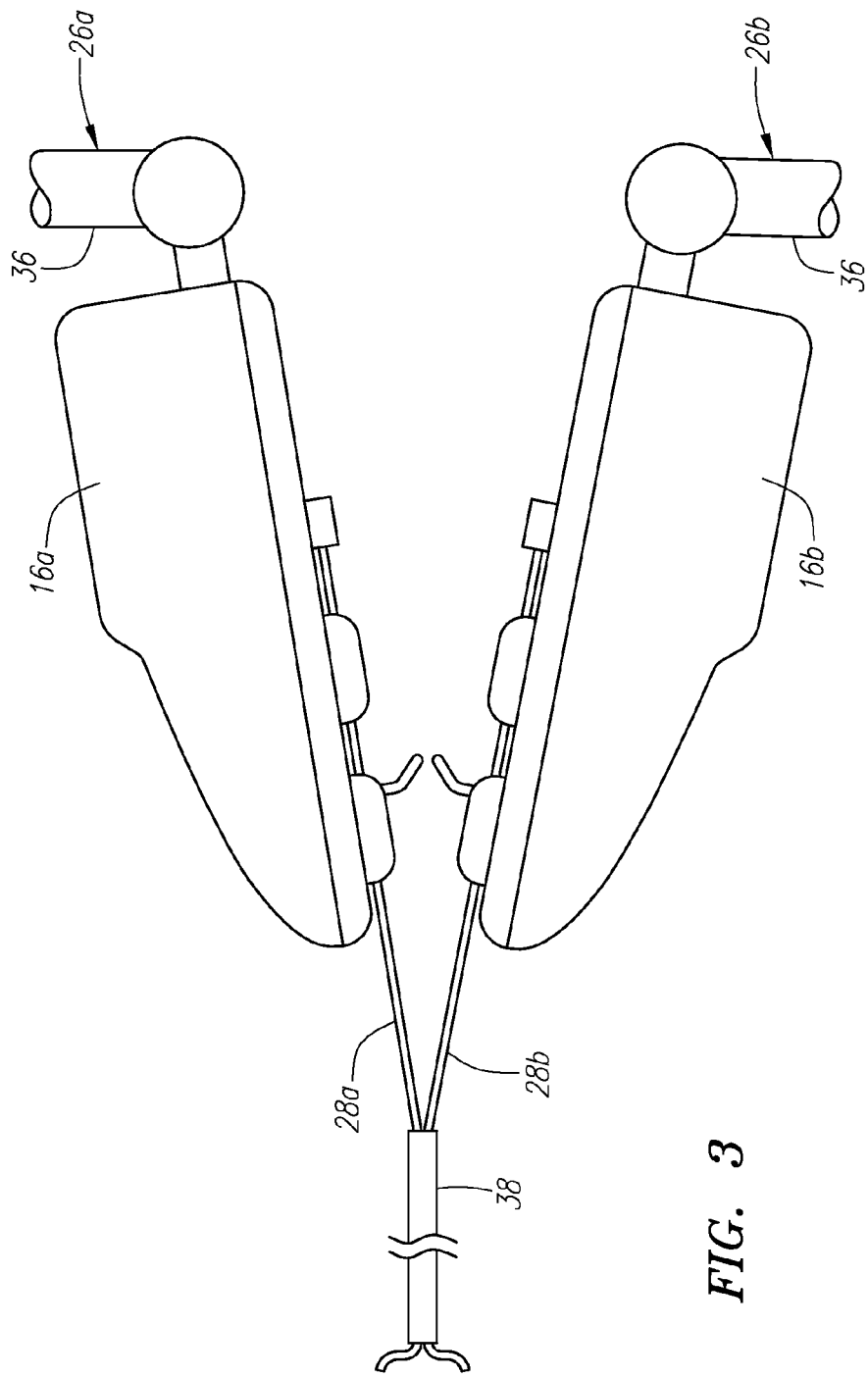
FIG. 3 illustrates another embodiment of a robotic catheter system in accordance with the present invention.

FIG. 3A depicts another embodiment of a robotic catheter system 30 comprising first and second support assemblies (26a and 26b) which are coupled to opposite sides of an operating table. This configuration may be advantageous for certain procedures where the instrument drivers (16a and 16b) can be located in positions not achievable with the embodiments of FIG. 1A, 1B or 2A-2E, for example.

Figure 4:
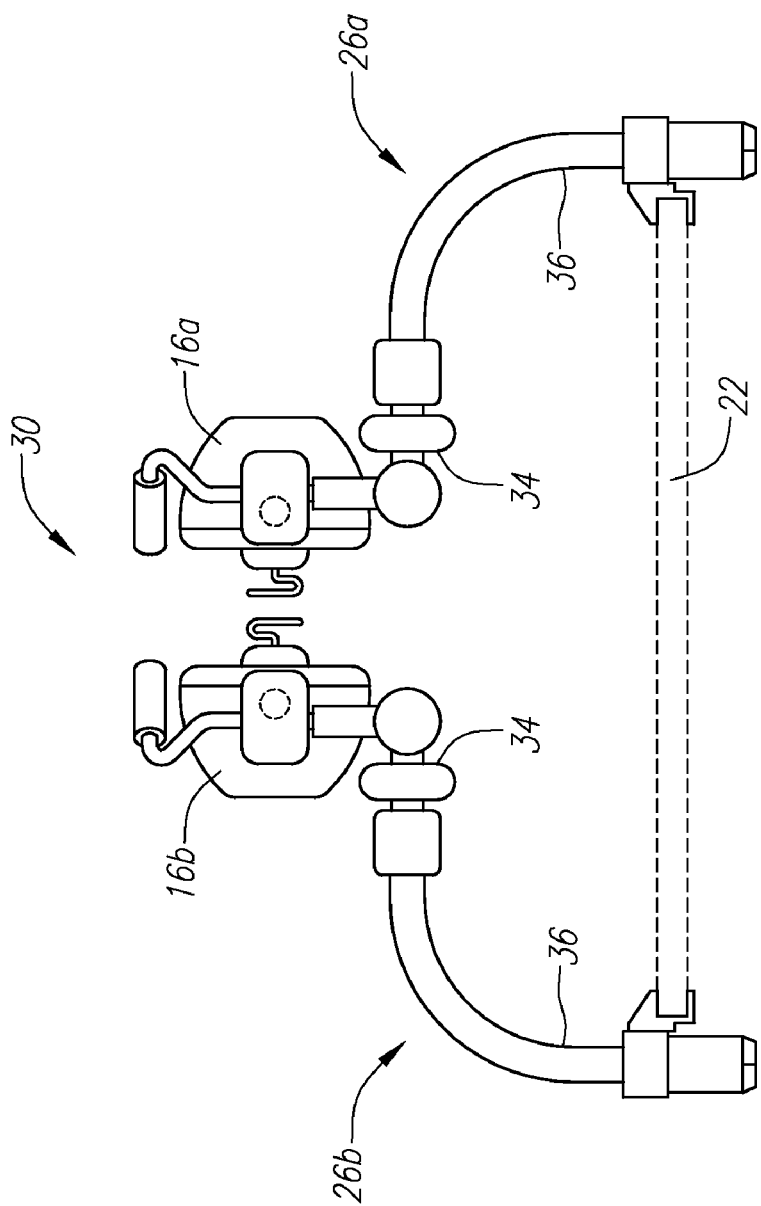
FIG. 4 illustrates another embodiment of a robotic catheter system in accordance with the present invention.

FIG. 4 depicts a close-up of a configuration of two instrument drivers (16a and 16b) with instrument assemblies (28a and 28b) positioned into a single introducer sheath (38). This configuration may be achieved utilizing a configuration of support assemblies (26a and 26b) such as that depicted in FIG. 3A, but is not limited to such embodiment. The single introducer sheath (38) may be the same or similar to the larger or "parent" endoscopic instrument as described in U.S. patent application Ser. No. 11/637,951. The single introducer sheath (38) may also be steerable, or non-steerable, or even robotically steerable using another instrument driver 16.

Figure 5A:
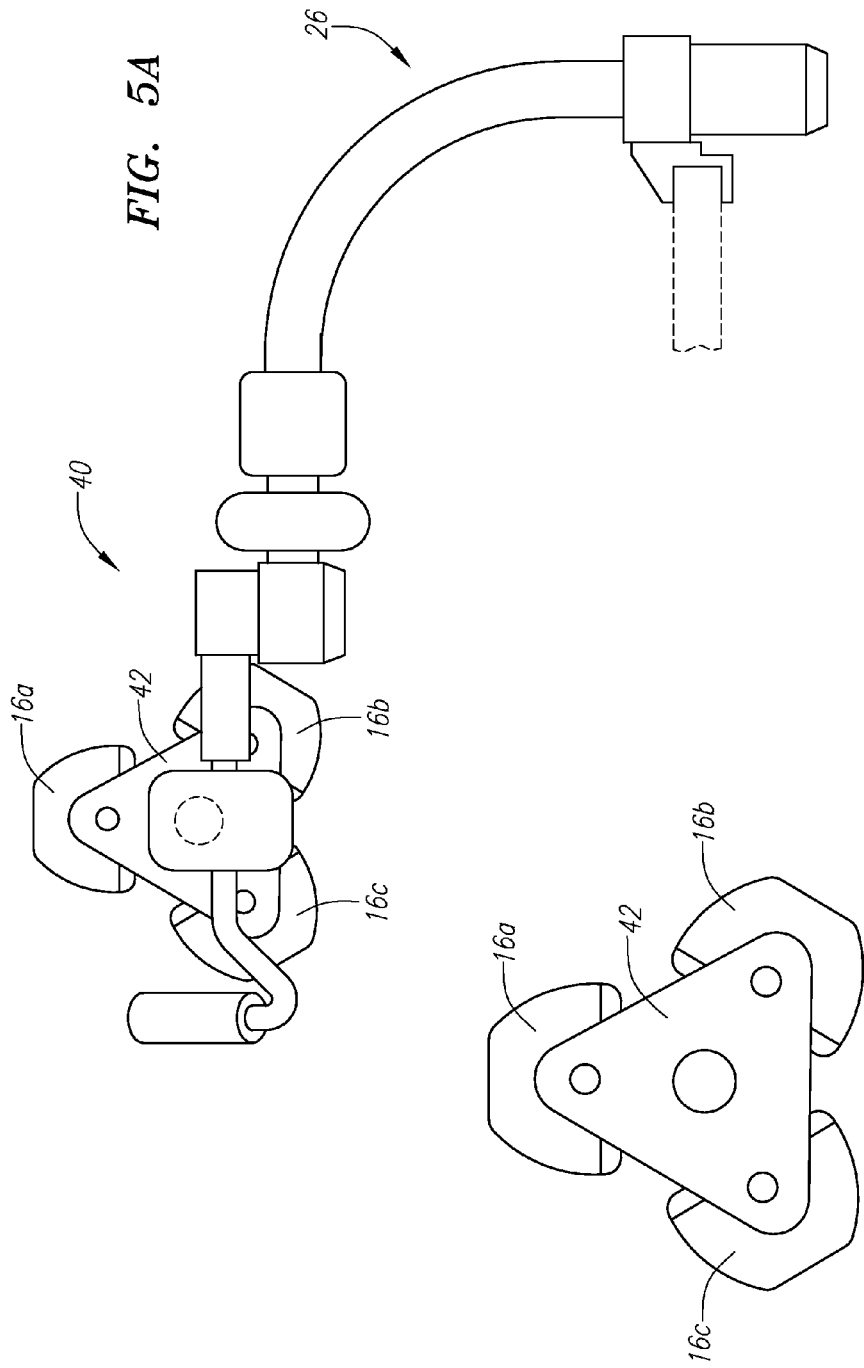
FIGS. 5A-5B illustrate another embodiment of a robotic catheter system in accordance with the present invention.
Figure 5B:
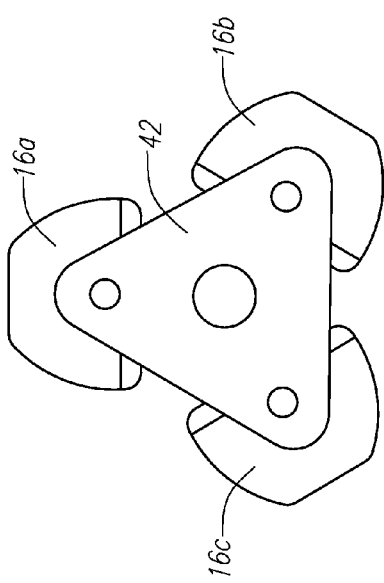

FIG. 5A depict another embodiment of a robotic catheter system 40 comprising a multi-instrument-driver 16 configuration capable of supporting three instrument drivers (16a, 16b and 16c) in a configuration such as that shown more closely in FIG. 5B. The instrument drivers 16 are coupled to a mounting assembly 42 which is in turn coupled to a support assembly 26. The mounting assembly 42 may be rotatably coupled or otherwise adjustably coupled (e.g. using a gimbal) to the support assembly to allow positional adjustment of the instrument drivers 16. In addition, the instrument drivers 16 may be adjustably coupled to the mounting assembly 42 to allow positional adjustment of the instrument drivers 16.

FIGS. 6 through 22 illustrate various, non-limiting intracardiac systems and procedures which may utilize any of the robotic catheter systems (10, 20, 30 and 40) described above to guide and operate the depicted instrument configurations inside of the patient (3).

Figure 6A:
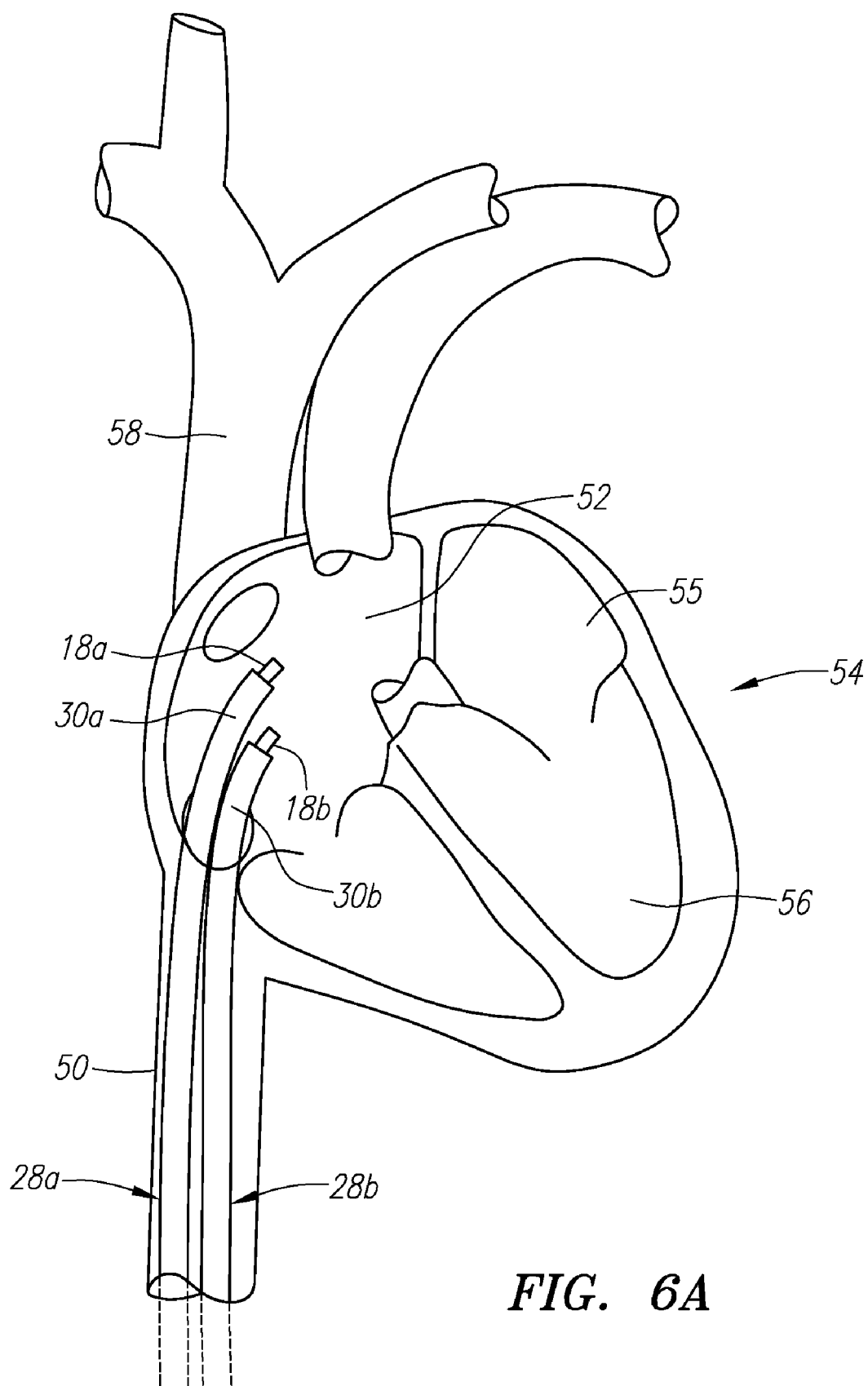
FIGS. 6A-6B illustrate embodiments of an intracardiac system and procedure according to the present invention.

Referring to FIG. 6A, a patient heart (54) comprises a right atrium (52), a left atrium (55), a left ventrical (56), an inferior vena cava (50), and a superior vena cava (58). According to the system and procedure of FIG. 6A, first and second instrument assemblies (28a and 28b) may be positioned through the inferior vena cava (50) and into the right atrium (52). The first instrument assembly (28a) comprises a sheath instrument (30a) and guide instrument (18a), while the second instrument assembly (28b) comprises a second sheath instrument (30b) and a second guide instrument (18b). The first and second instrument assemblies (28a and 28b) may then be operated to perform a medical procedure (e.g. a diagnostic or interventional procedure) within the patient's heart.

Figure 6B:
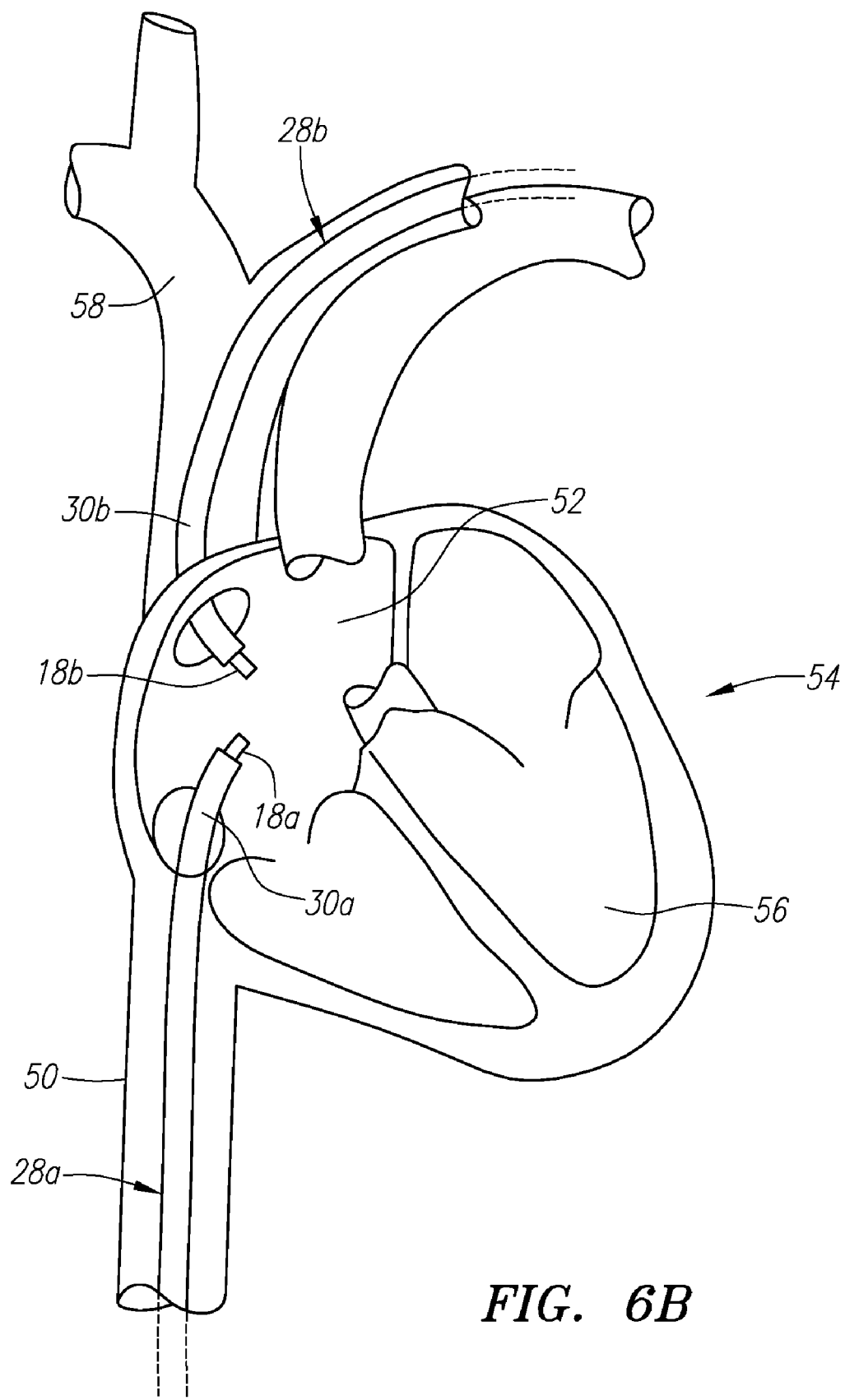

FIG. 6B depicts a similar configuration to FIG. 6A, but with one of the instrument assemblies (28b) entering the right atrium (52) via the superior vena cava (58), as may be preferred for clinical reasons. In the depictions of embodiments that follow, various combinations of such entry configurations are utilized for illustration purposes.

Figure 7:
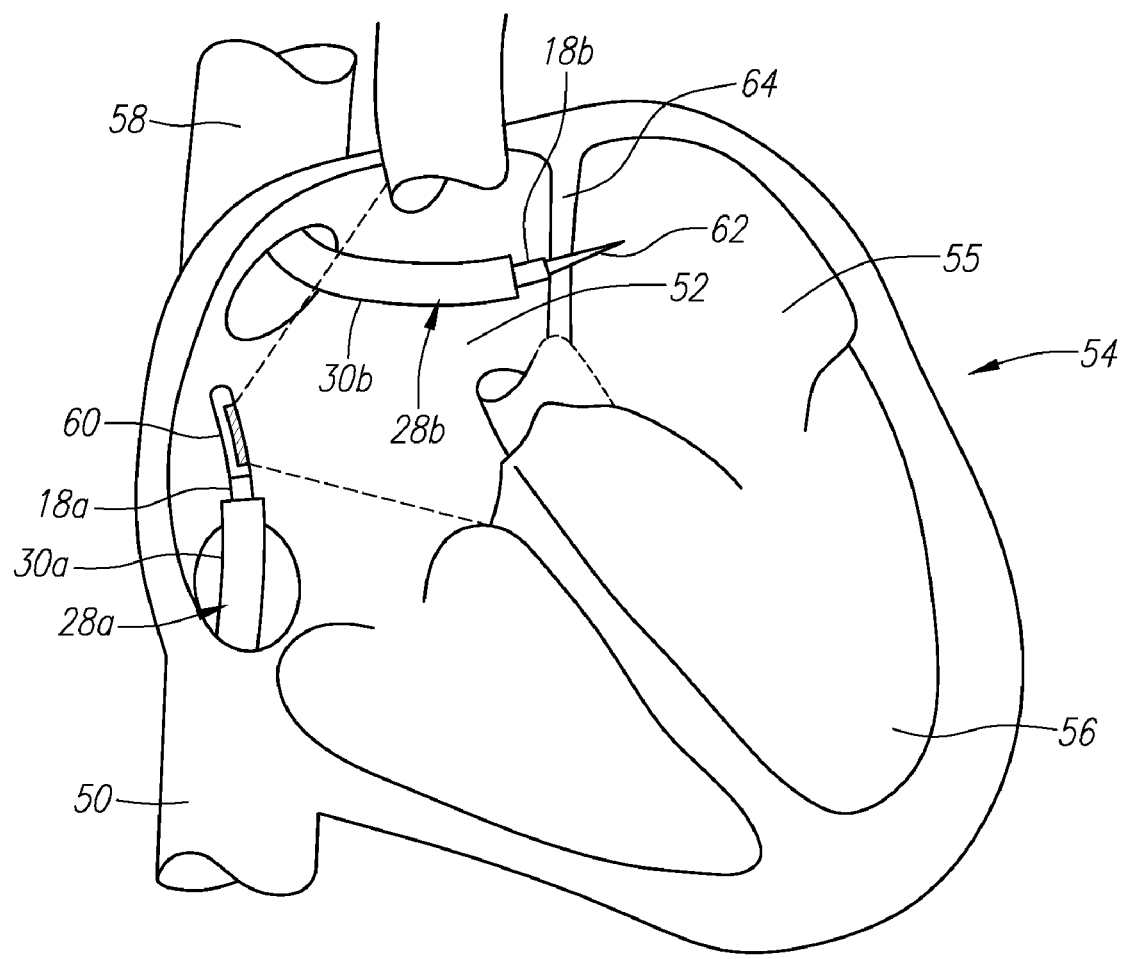
FIG. 7 illustrates another embodiment of an intracardiac system and procedure according to the present invention.

Referring to FIG. 7, a first instrument assembly (28a) comprising a sheath instrument (30a) and a guide instrument (18a) having an intracardiac echocardiography ("ICE") catheter (60) positioned through the distal end of the guide instrument (18a). The first instrument assembly (28a) is utilized to position the ICE in a preferred position with a directed field of view (shown by the dashed lines in FIG. 7). A second instrument assembly (28b) comprising a second guide instrument (18b) and a second sheath instrument (30b) may be utilized to drive a needle (62) with great precision through the atrial septum (64). The first instrument assembly (28a) may be positioned in the heart (54) through the inferior vena cava (50), while the second instrument assembly (28b) accesses the heart (54) through the superior vena cava (58), or vice versa, or both instrument assemblies may be positioned through either the superior vena cava (58) or the inferior vena cava (50), as shown in the embodiment of FIGS. 8A-8B.

Figure 8A:
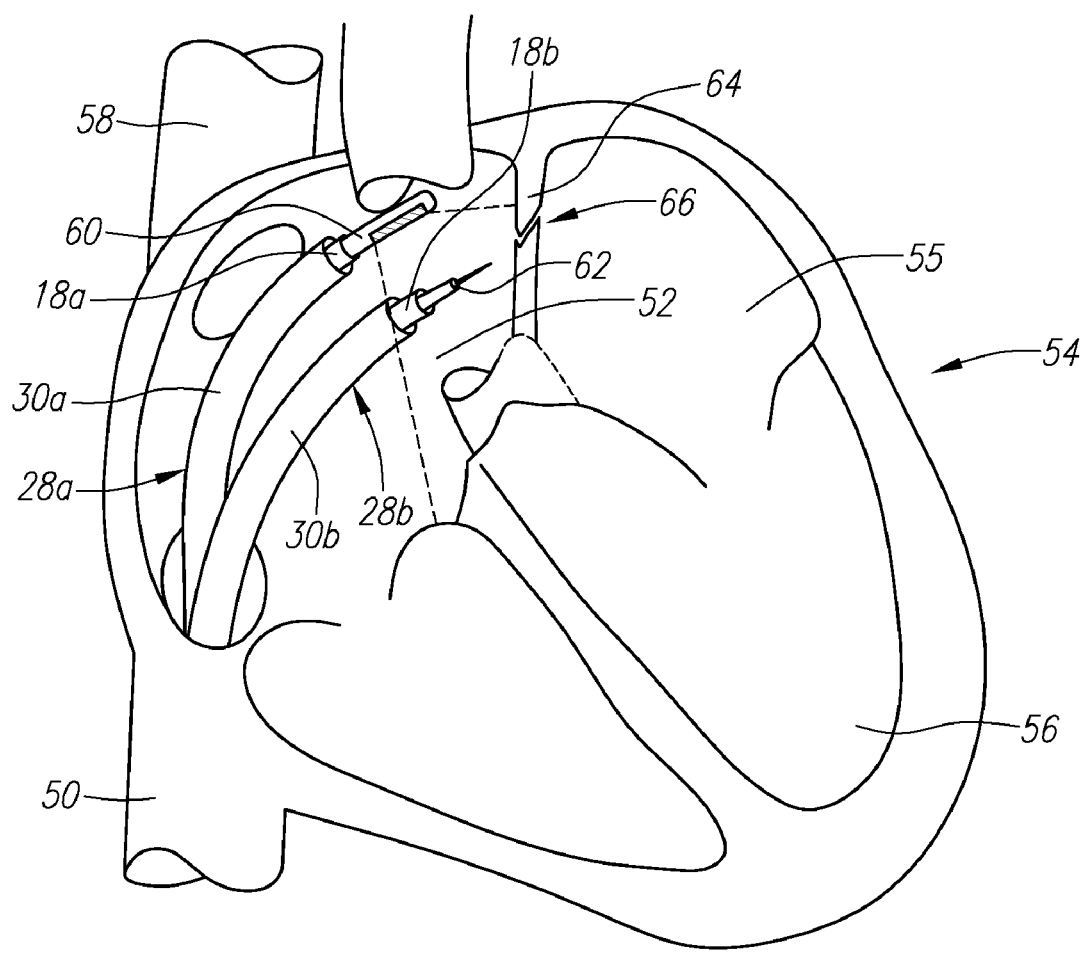
FIGS. 8A-8B illustrate another embodiment of an intracardiac system and procedure according to the present invention.
Figure 8B:
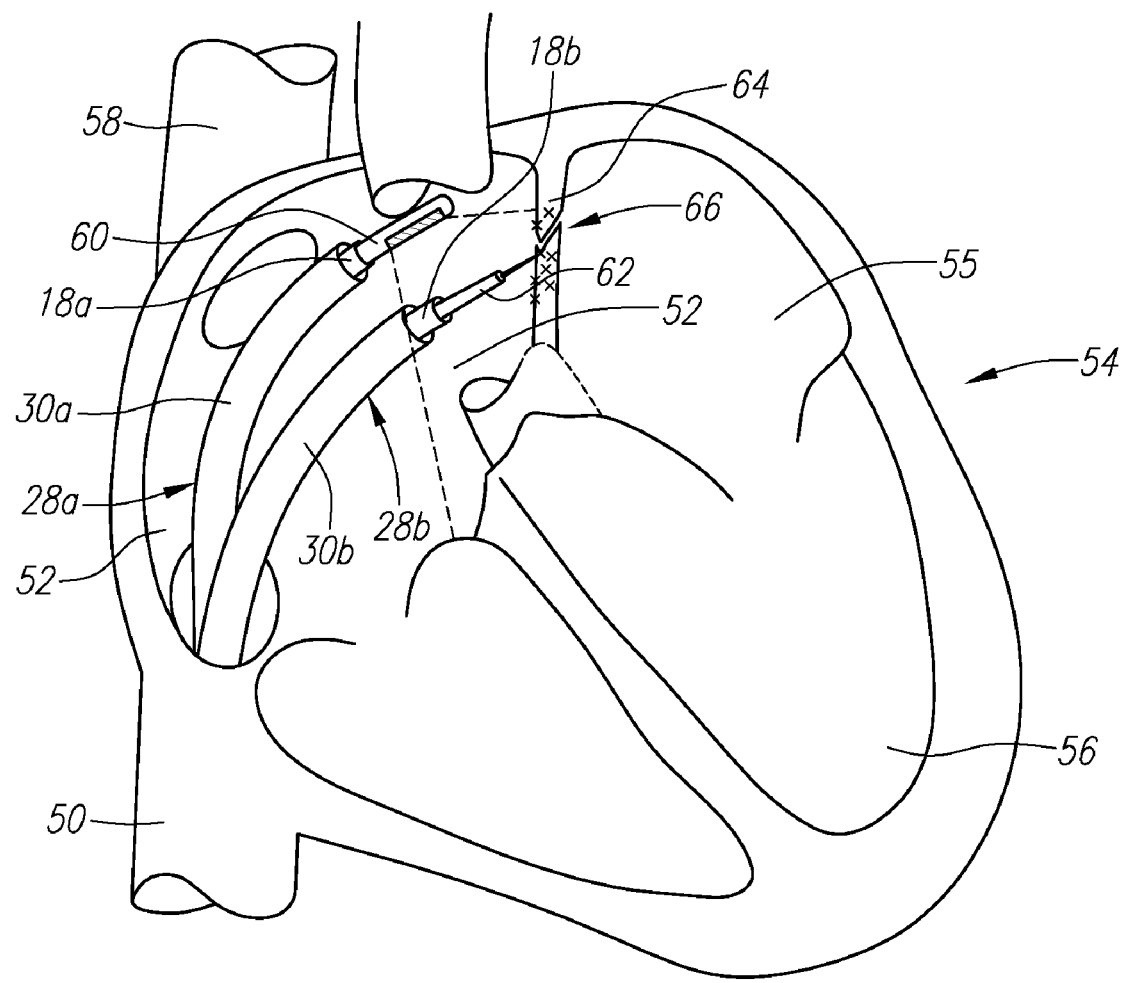

Referring to FIGS. 8A-8B, another embodiment of an intracardiac system and procedure may be utilized to produce injury or irritation around a patent foramen ovale ("PFO") (66) to induce healing and closure of such PFO. With reference first to FIG. 8A, a first instrument assembly (28a) having an ICE catheter (60) positioned through the distal end of the guide instrument (18a) may be positioned in the heart (54) through the inferior vena cava (50). A second instrument assembly (28b) also accesses the heart (54) through the inferior vena cava (58). An instrument having a needle (62) is positioned through the guide instrument (18b). The ICE (60) may be used to produce an image of the surgical site (i.e. the area around the atrial septum (64)) in order to facilitate the procedure. Turning to FIG. 8B, the needle is driven into the atrial septum (64) around the PFO to induce healing and closure of the PFO.

Figure 9:
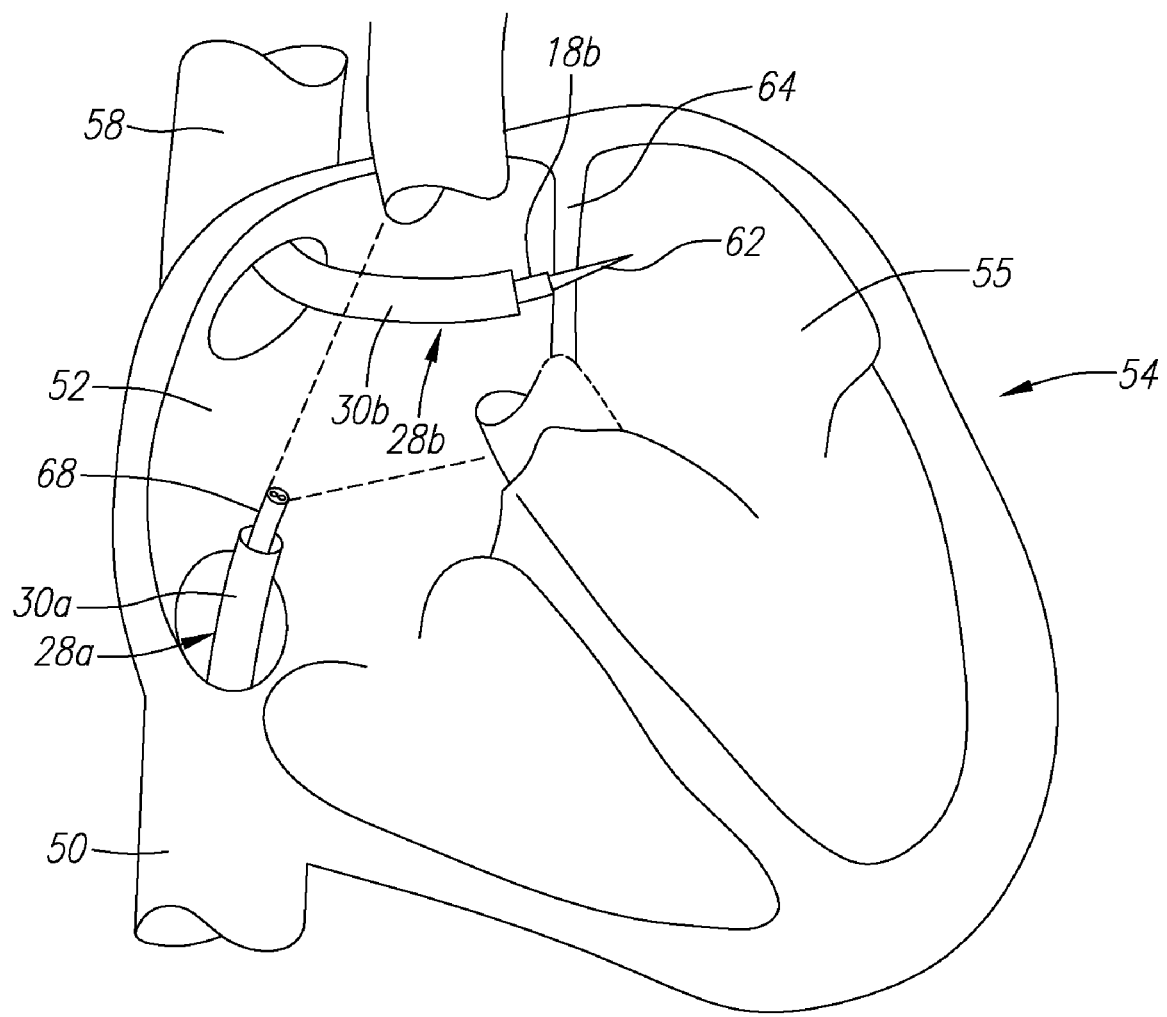
FIG. 9 illustrates another embodiment of an intracardiac system and procedure according to the present invention.

FIG. 9 illustrates still another embodiment of an intracardiac system and procedure which is an embodiment for PFO closure similar to FIGS. 8A-8B, except that is utilizes an infrared image capture device (68) positioned through the guide catheter (18a) and the second instrument assembly (28b) is positioned in the heart (54) through the superior vena cava (58). The infrared image capture device (68) may be disposed on the distal end of the first instrument guide (18a), or it may be a separate catheter inserted through the first instrument guide (18a).

Figure 10:
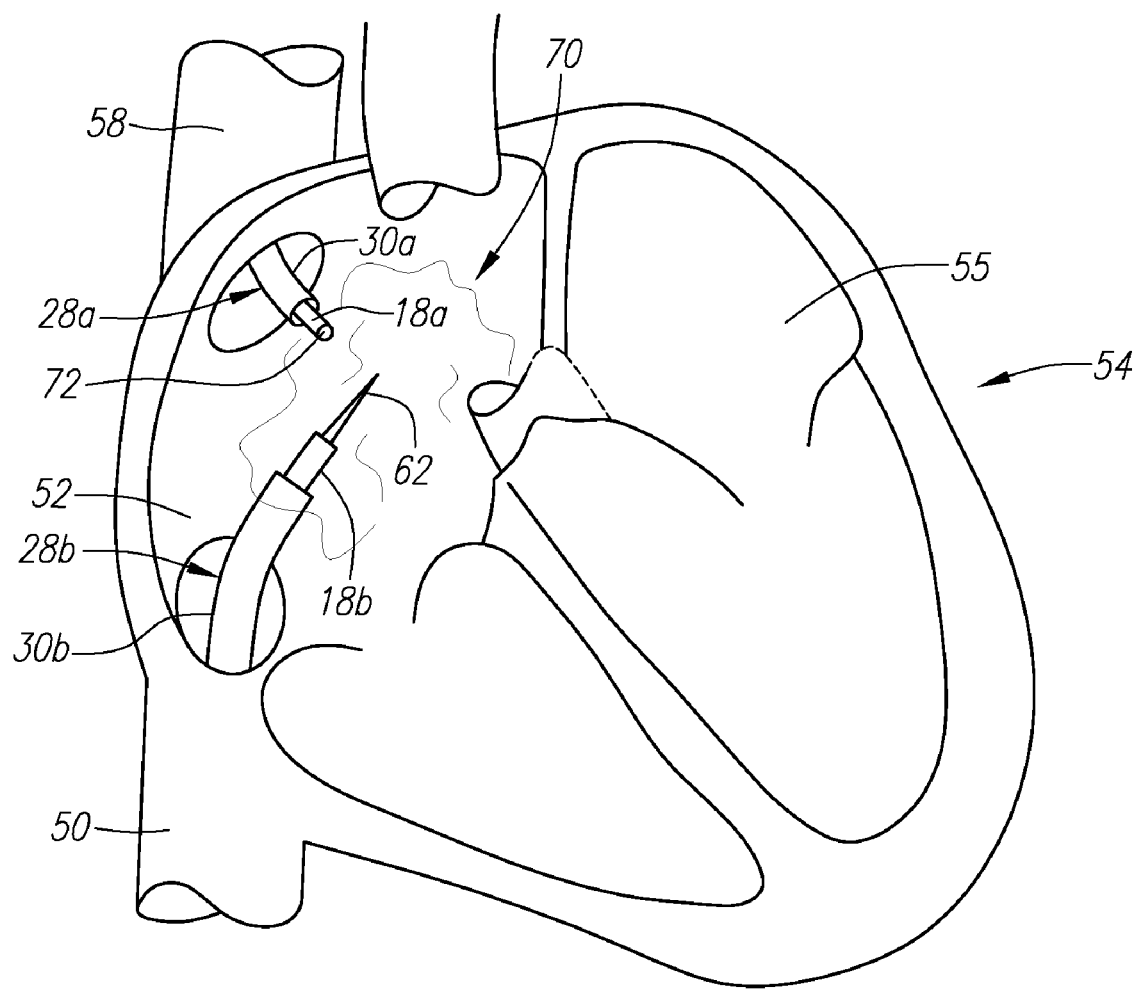
FIG. 10 illustrates another embodiment of an intracardiac system and procedure according to the present invention.

Referring to FIG. 10, another embodiment of an intracardiac system and procedure utilizes a contrast agent (70) injected through an irrigation port (72) in a first instrument assembly (28a) to produce quality fluoroscopic images of the pertinent volume, such as the right atrium (52). This system and procedure may also be used to perform a PFO closure as described above, or other suitable procedure.

Figure 11:
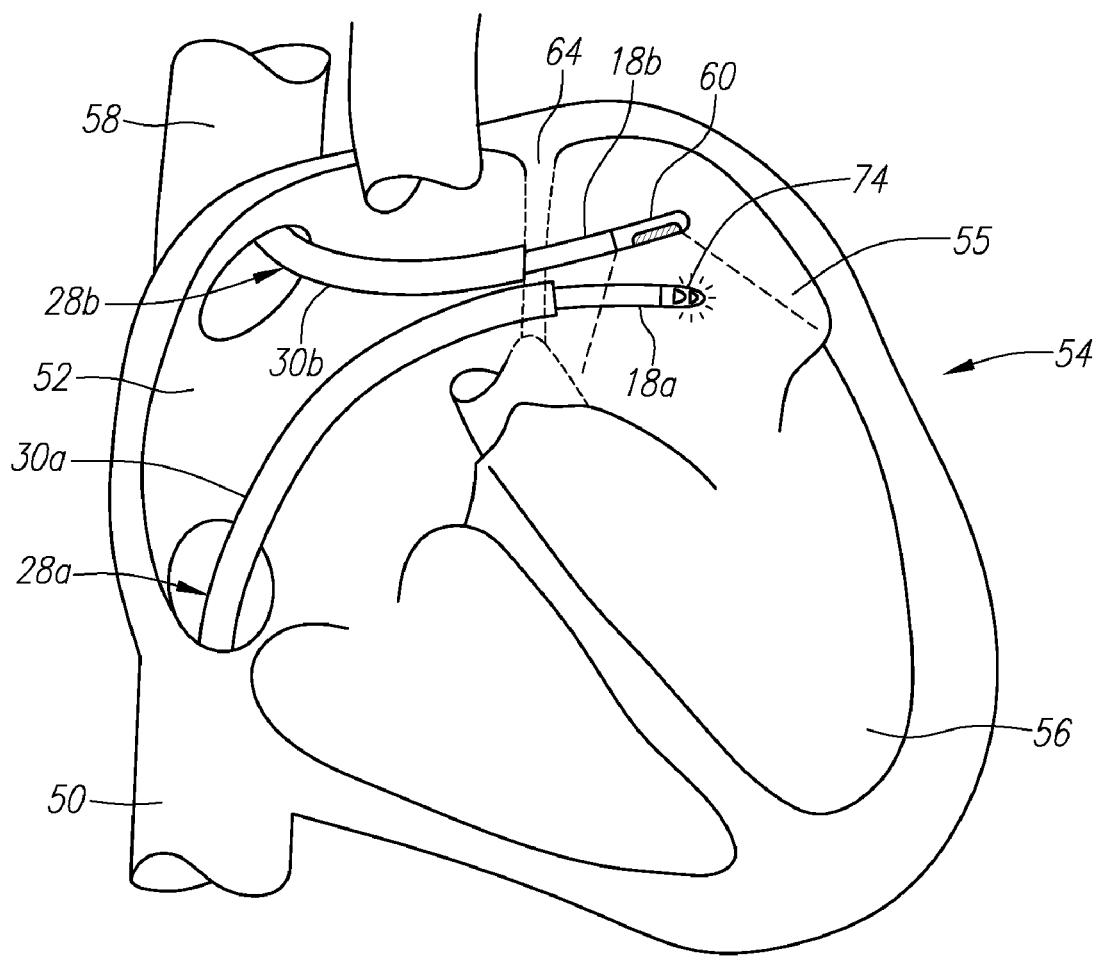
FIG. 11 illustrates another embodiment of an intracardiac system and procedure according to the present invention.

Referring to FIG. 11, in yet another embodiment of an intracardiac system and procedure, the first instrument assembly (28a) and second instrument assembly (28b) may be navigated transseptally (through the atrial septum (64)). In this embodiment, an ICE catheter (60) disposed on the second instrument assembly (28b) is robotically navigated into a preferred position adjacent an ablation catheter (74) disposed on the first instrument assembly (28a). Once in position, the ablation catheter (74) may be utilized to ablate tissue lesions in the left atrial (55) wall.

Figure 12:
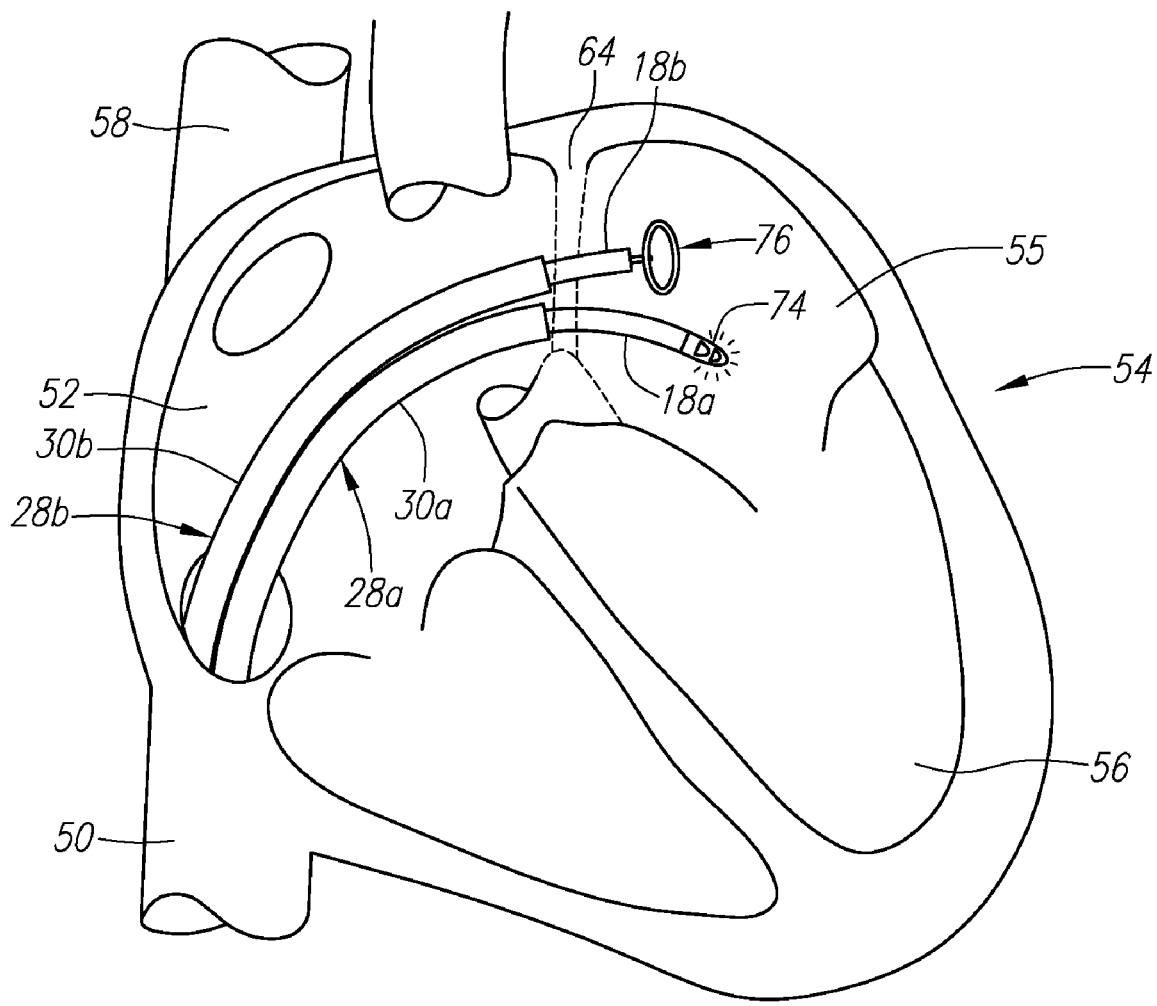
FIG. 12 illustrates another embodiment of an intracardiac system and procedure according to the present invention.

FIG. 12 depicts another embodiment of an intracardiac system and procedure for lasso mapping and ablation, for example, for treating an arrhythmia. The first instrument assembly (28a) and second instrument assembly (28b) are navigated transseptally, similar to the embodiment of FIG. 11. The first instrument assembly (28a) comprises an ablation catheter (74) and/or an imaging catheter (60). A lasso catheter (76) is disposed on the second instrument assembly (28b). A lasso catheter (76) is a device which can be used to map the electric signal from tissues. Biosense Webster sells an exemplary lasso catheter (76).

Figure 13A:
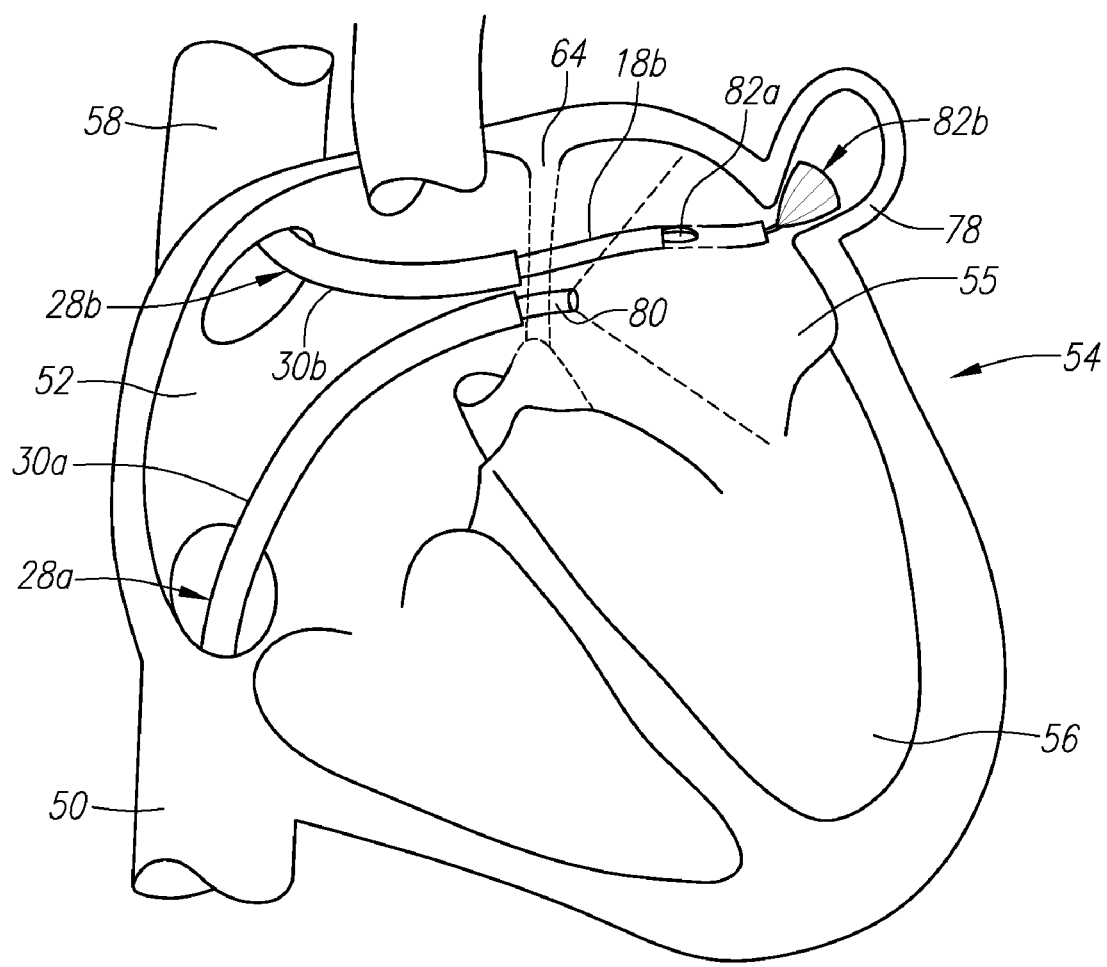
FIGS. 13A-13D illustrate another embodiment of an intracardiac system and procedure according to the present invention.

Referring now to FIGS. 13A-13D, in another embodiment of an intracardiac system and procedure, similar configurations may be utilized to treat a left atrial appendage (78) ("LAA"). Turning first to FIG. 13A, the first instrument assembly (28a) is provided with an image capture device (80), such as an ultrasound imaging device, camera, infrared camera, or the like. The second instrument assembly (28b) is adapted to deliver an LAA occupying prosthesis (82), such as those available from AtriTech, Inc. The prosthesis (82) is first delivered in an unexpanded state as shown in FIG. 13A as (82a). The image capture device (80) is directed at the LAA (78) in order to facilitate placement of the prosthesis using the second instrument assembly (28b). The prosthesis (82) is inserted into the LAA (78) using the second instrument assembly (28b) and the prosthesis (82) expands in the LAA (78) thereby filling the LAA (78) and relieving the stress on the atrial wall, as shown as (82b).

Figure 13B:
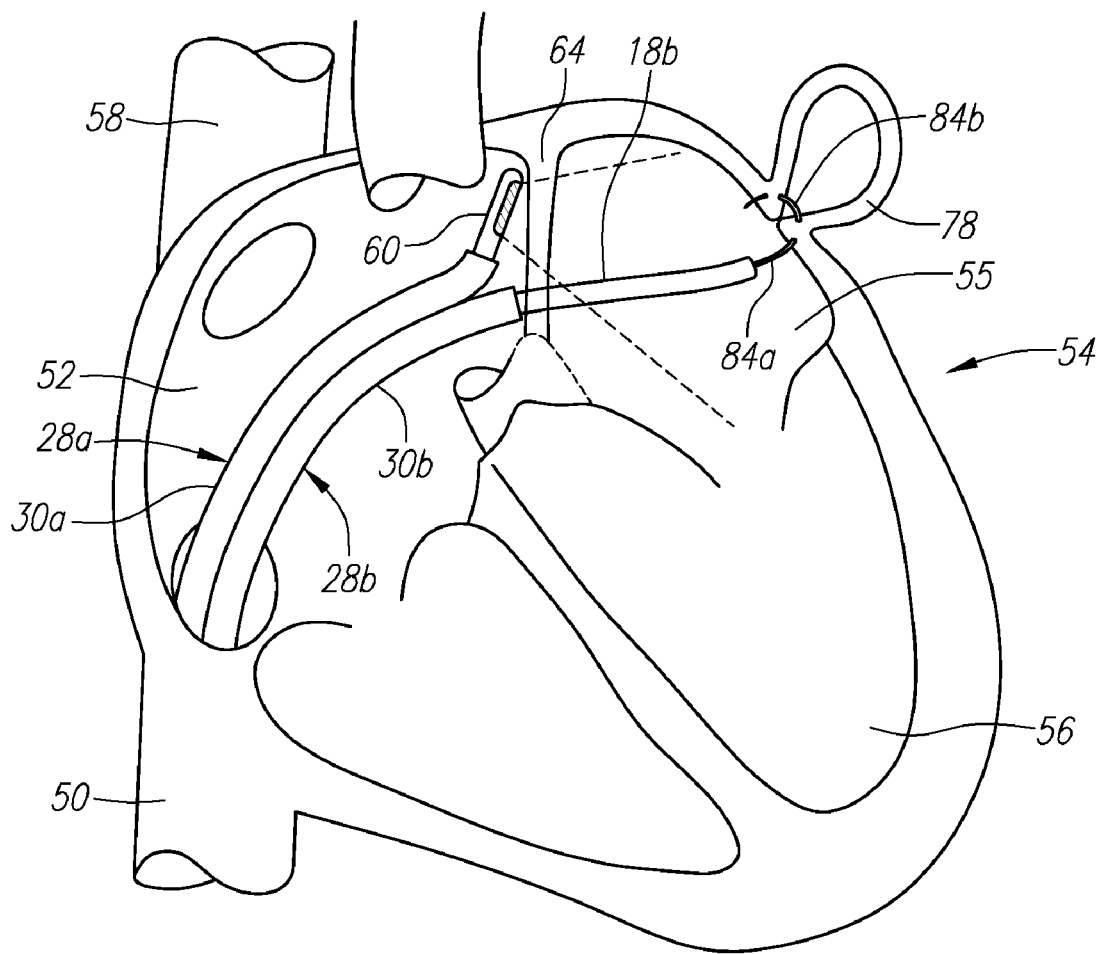
Figure 13C:
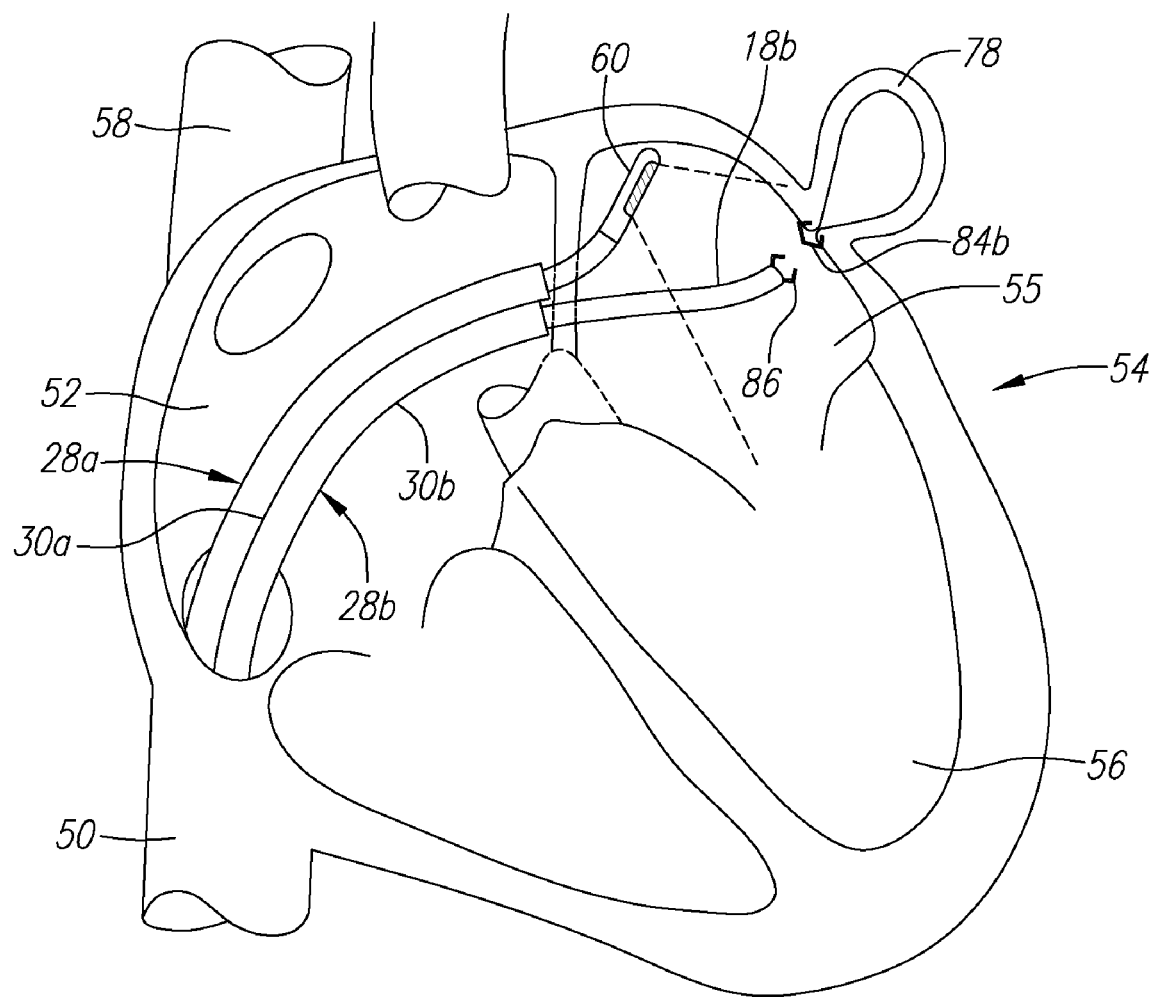

Turning to FIG. 13B, an LAA (78) is treated by deploying a nitinol clip (84), such as those manufactured by Coalescent Surgical, Inc. In this embodiment, the second instrument assembly (28b) is adapted to deliver the nitinol clip (84) and the first instrument assembly (28a) is provided with an ICE for assisting in locating the LAA (78). The second instrument assembly (28b) is used to deploy the nitinol clip (84) to close the LAA (78), as depicted in FIG. 11B. The embodiment shown in FIG. 11C is substantially the same as that shown in FIG. 11B, except that the second instrument assembly (28b) is also provided with a clip applier (86) to facilitate deployment of the nitinol clip (84). The nitinol clip (84) is shown as undeployed at (84a) and as it is deployed to close the LAA at (84b).

Figure 13D:
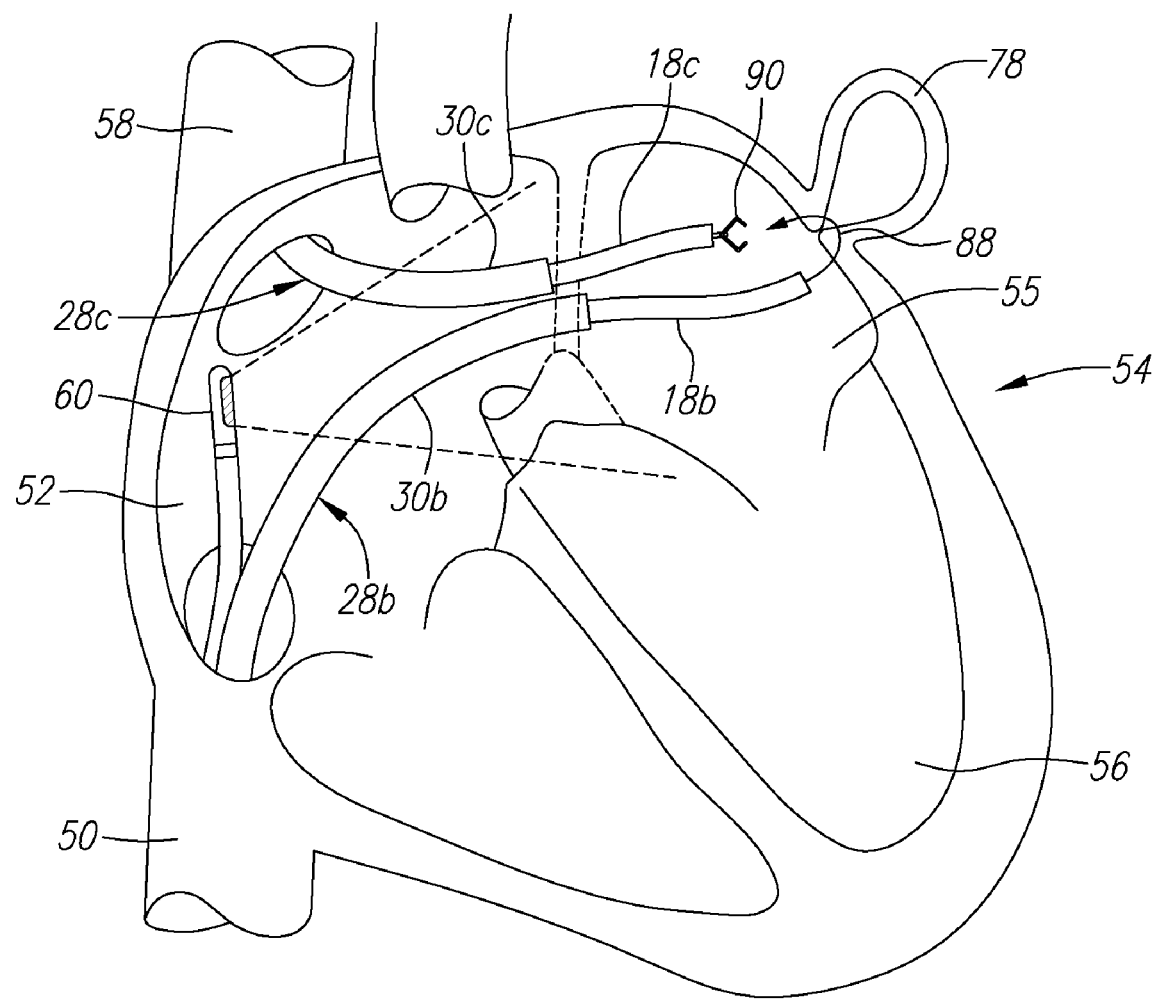

FIG. 13D depicts yet another embodiment of an LAA (78) repair wherein the second instrument assembly is provided with a needle and suture complex (88). The first instrument assembly (28a) is provided with an ICE (60) similar to the embodiments of FIGS. 13B and 13C. Alternative to a first instrument assembly (28a), the ICE catheter may be a stand-alone catheter separate from the robotic catheter system. In addition, a third instrument assembly (28c) having a grasping tool (90) is utilized. The second instrument assembly (28b) is used to pass the needle and suture complex (88) through the wall of the LAA (78) to the grasping tool (90). The third instrument assembly (28c) is used to operate the grasping tool (90) to grasp the needle of the complex (88) after it passes through the wall in order to apply tension to the suture complex (88) to close the LAA (78).

Figure 14A:
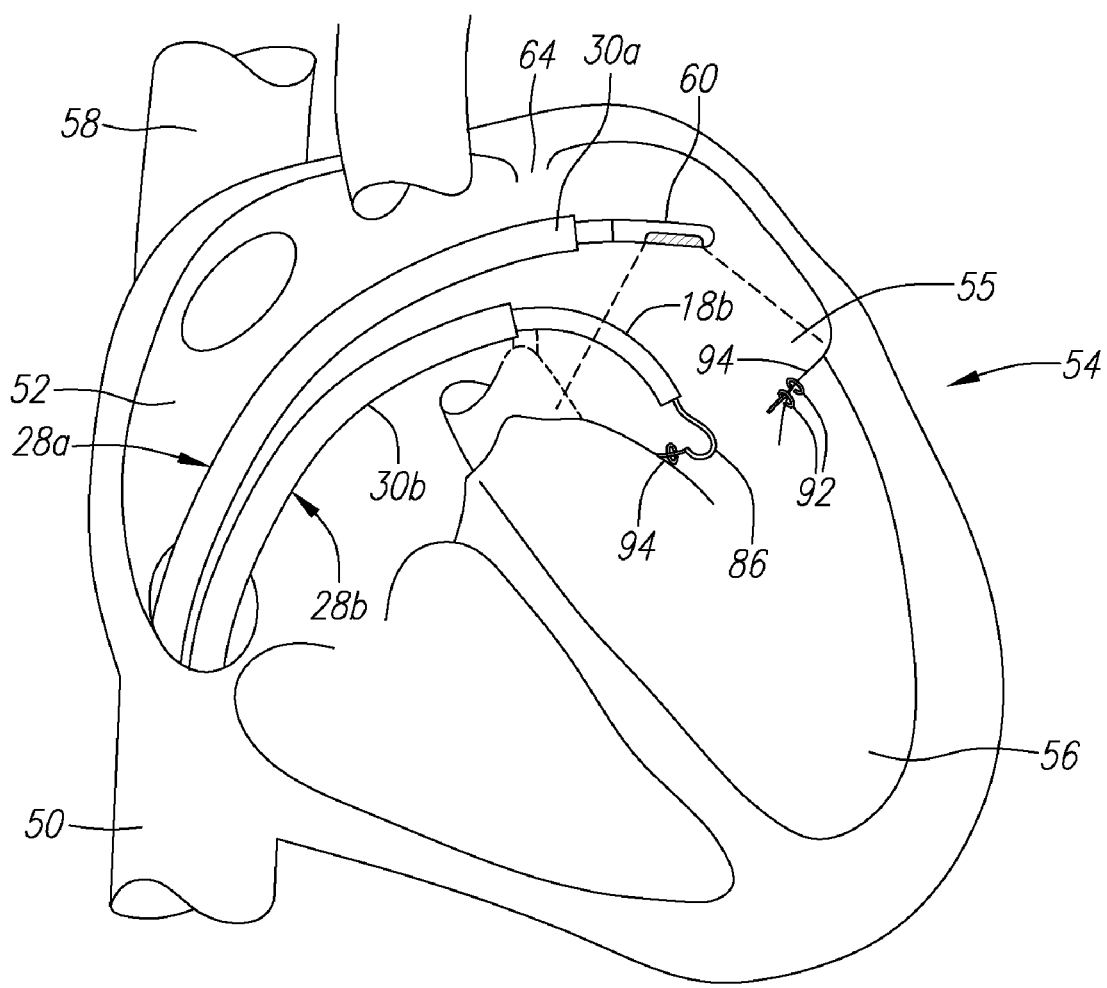
FIGS. 14A-14B illustrate another embodiment of an intracardiac system and procedure according to the present invention.
Figure 14B:
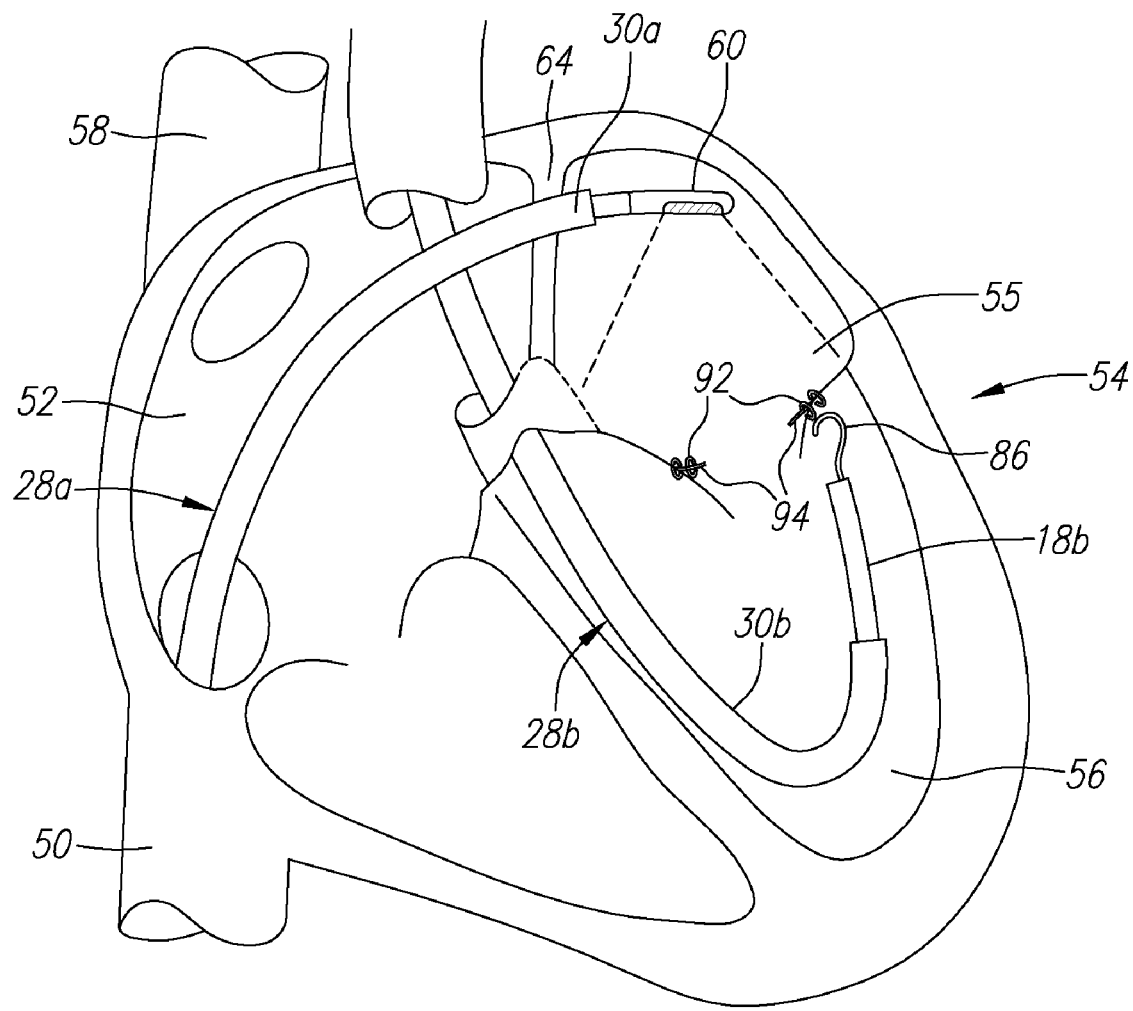

FIG. 14A-14B depict an embodiment of an intracardic system and procedure for performing a mitral valve repair using transseptal mitral annulus (94) geometry tuning by deploying clips (92) to the mitral annulus (94) with the help of ICE (60) imaging. The first instrument assembly (28a) includes an ICE (60) while the second instrument assembly (28b) has a clip applier (86). Utilizing the ICE (60) to facilitate the placement of the clips (92), the second instrument assembly (28b) and its clip applier (86) deploy one or more clips onto the mitral annulus (94). FIG. 12B depicts a retrograde approach for the same mitral valve repair. In the retrograde approach, the second instrument assembly (28b) is positioned in the left ventricle (56) such that instrument assembly (28b) approaches the mitral valve in the upstream direction of the flow of blood from the left atrium (55) to the left ventricle (56), thus referred to as "retrograde."

Figure 15A:
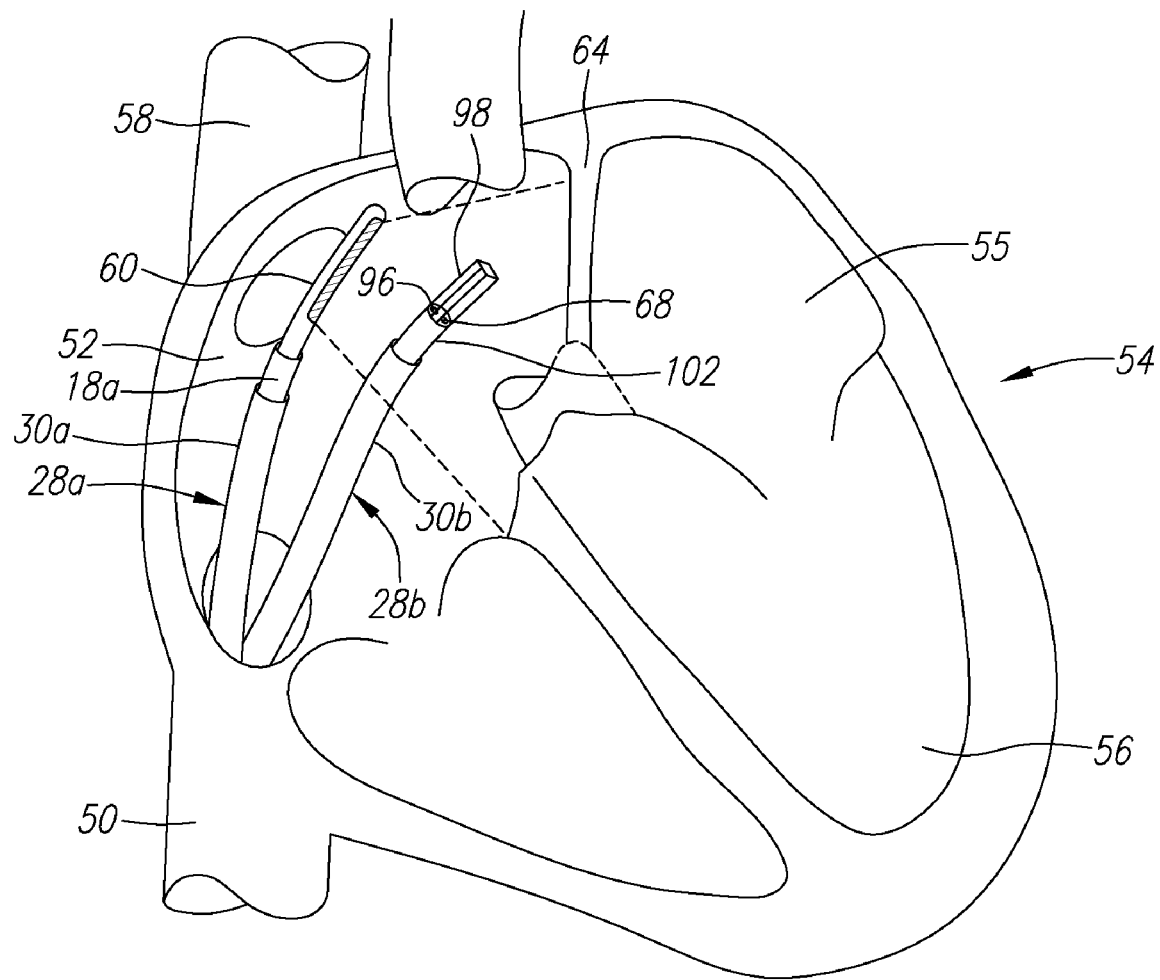
FIGS. 15A-15d illustrate another embodiment of an intracardiac system and procedure according to the present invention.
Figure 15B:
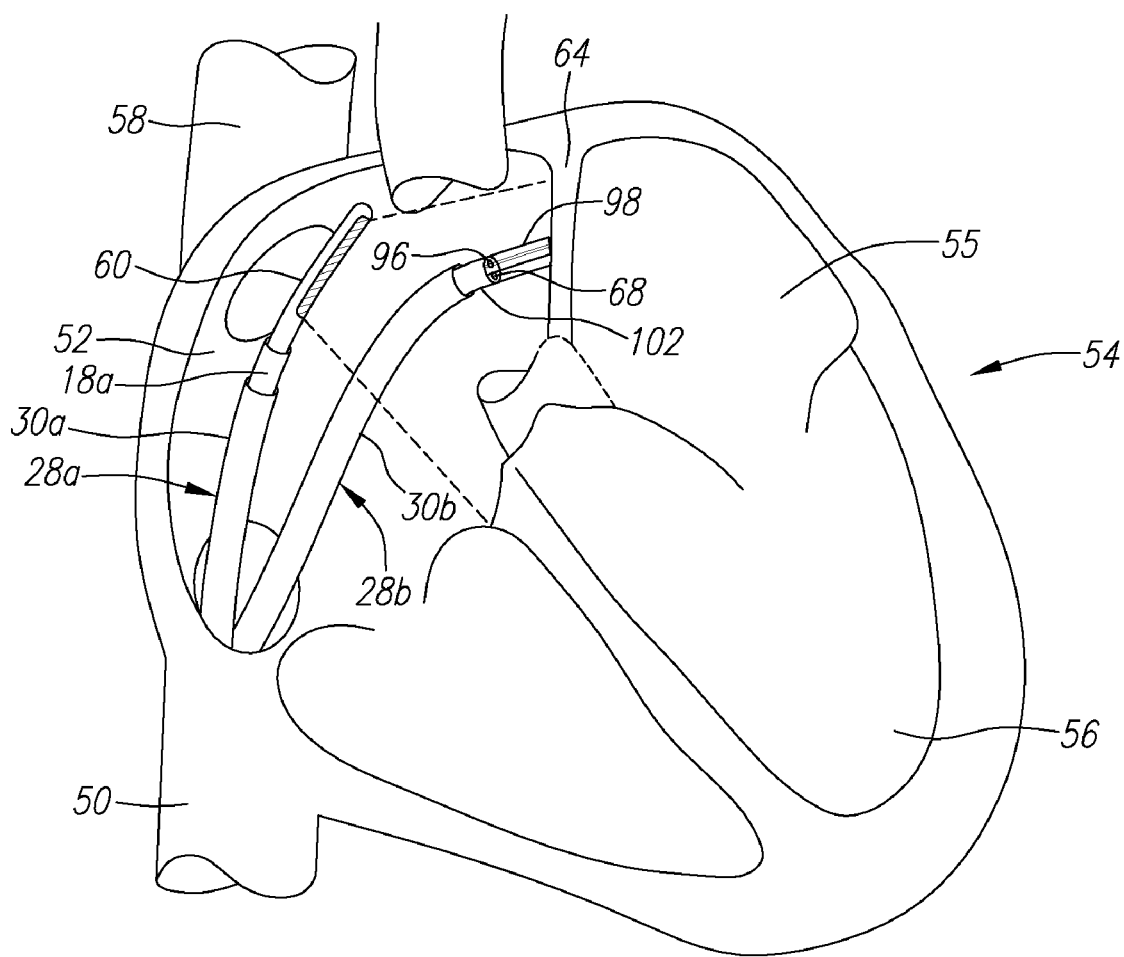
Figure 15C:
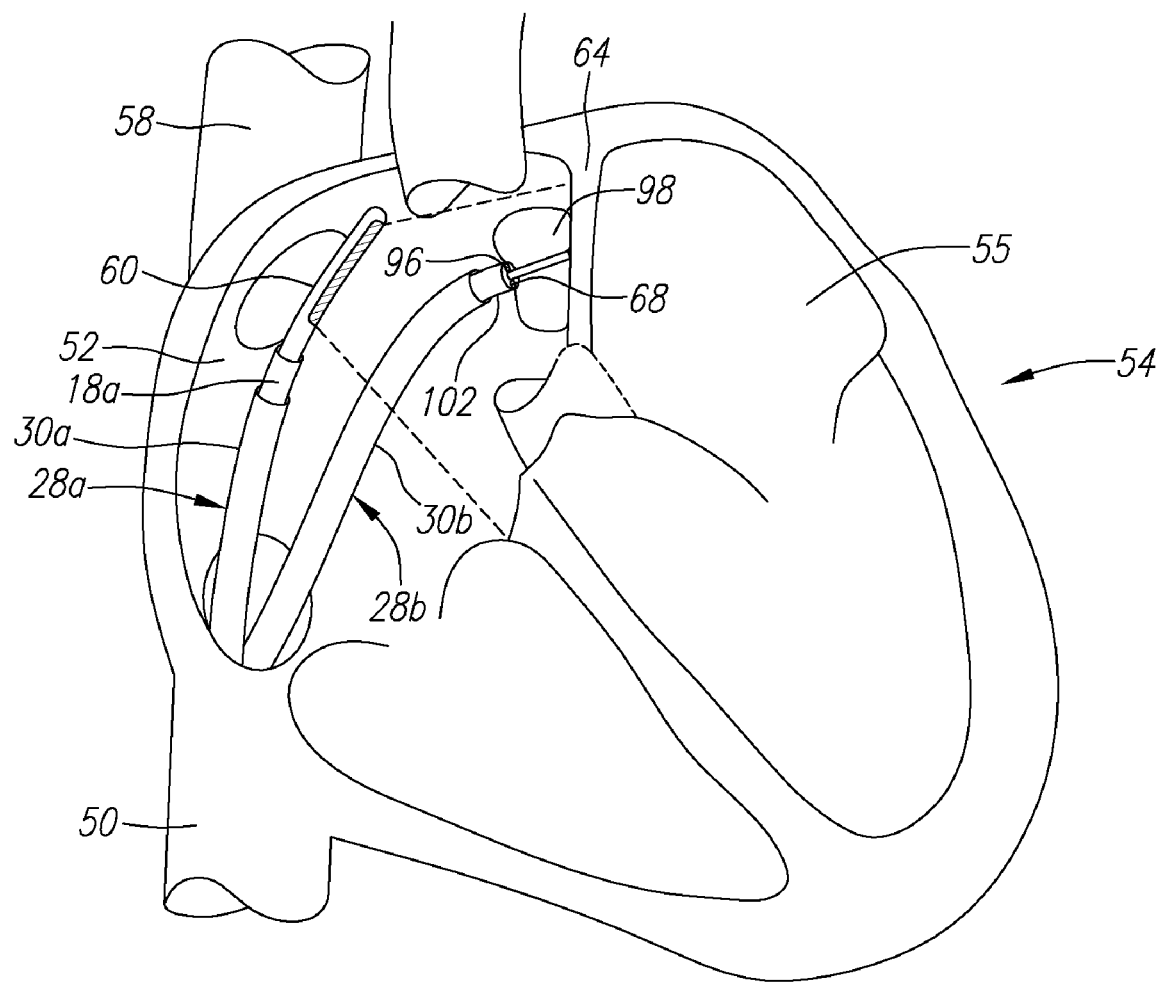
Figure 15D:
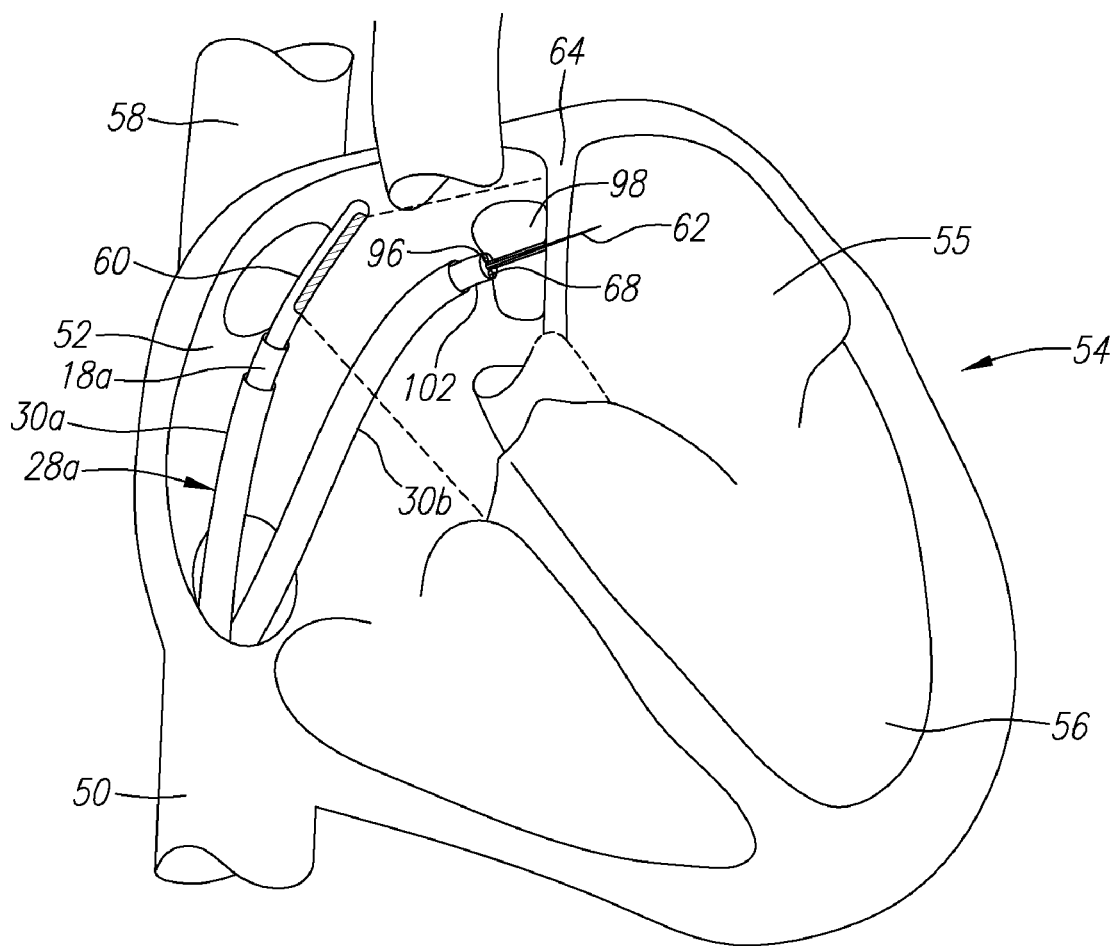

Referring to FIGS. 15A-15D, another embodiment of an intracardiac system and procedure is depicted for performing a transseptal perforation and crossing. The first instrument assembly (28a) includes an ICE (60). The second instrument assembly (28b) includes a cardioscopy catheter (102) having an image capture device (68), an irrigation port (96), a balloon (98) and a needle (62). The balloon (98) is preferably formed in an annulus shape about the needle (62) so that the needle (62) may be extended beyond the distal end of the balloon (98) without puncturing the balloon (98). The first instrument assembly (28a) is moved into position within the right atrium (52) to provide the ICE (60) with a field of view of the atrial septum (64), as shown in FIG. 15A. The first instrument assembly (28a) is maneuvered to position the uninflated balloon (98) into position against, or proximate, the atrial septum (64), as shown in FIG. 15B. As depicted in FIG. 15C, The balloon (98) is then inflated such that it bears against a relatively large area of the atrial septum (64), thereby stabilizing the distal end of the second instrument assembly (28b) and providing a clear field of view for the image capture device (68). Then, the needle (62) is extended to puncture through the atrial septum (64), as shown in FIG. 15D.

Figure 16A:
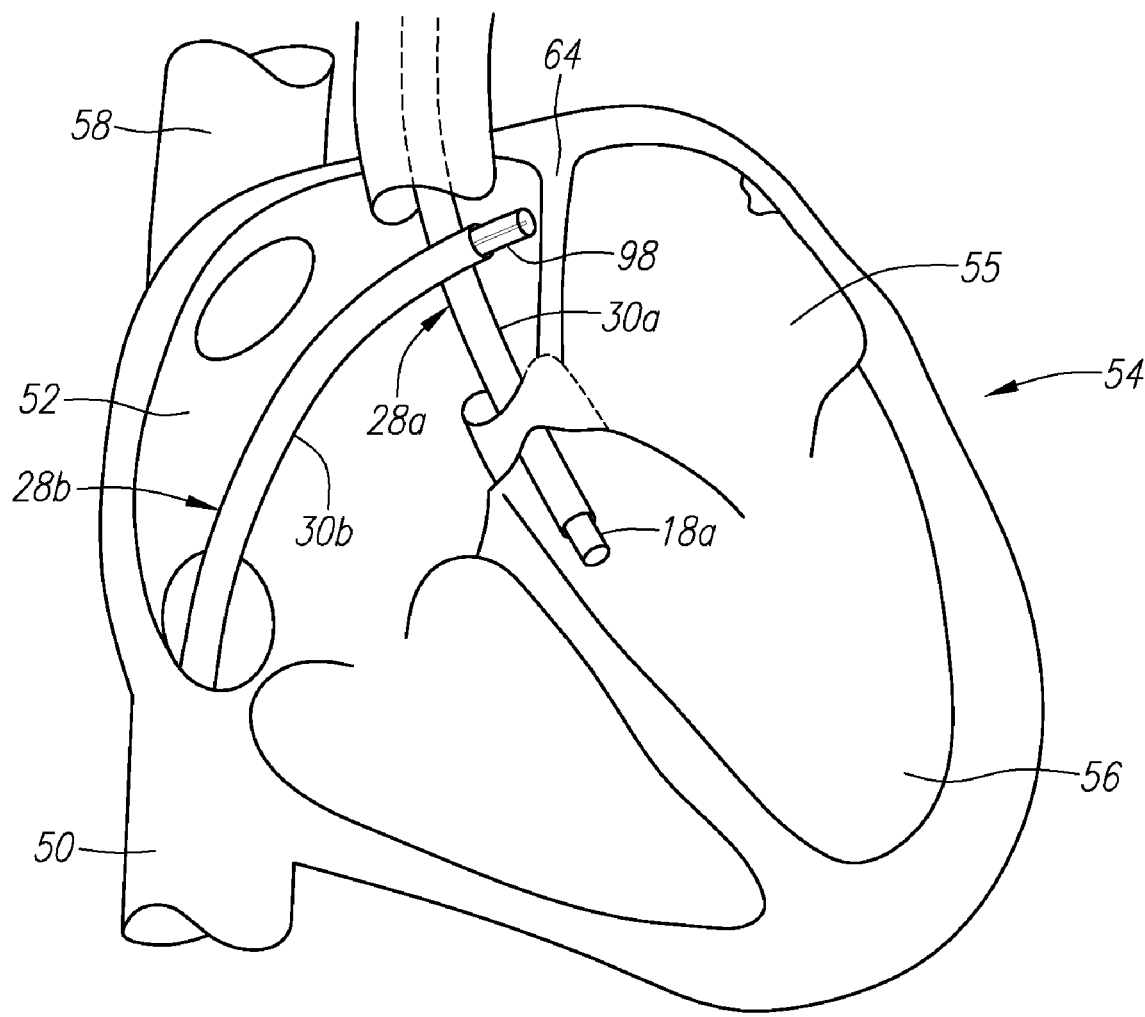
FIGS. 16A-16C illustrate another embodiment of an intracardiac system and procedure according to the present invention.
Figure 16B:
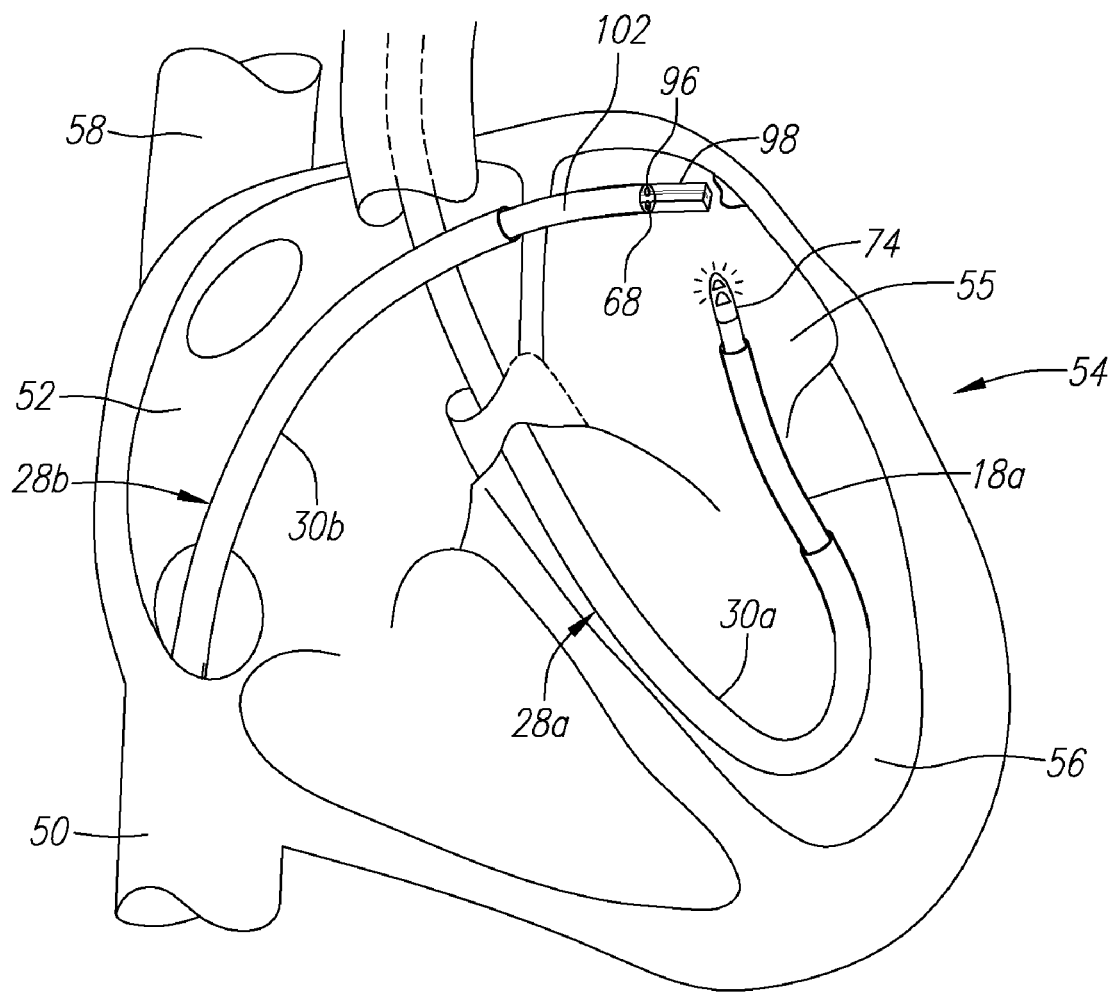
Figure 16C:
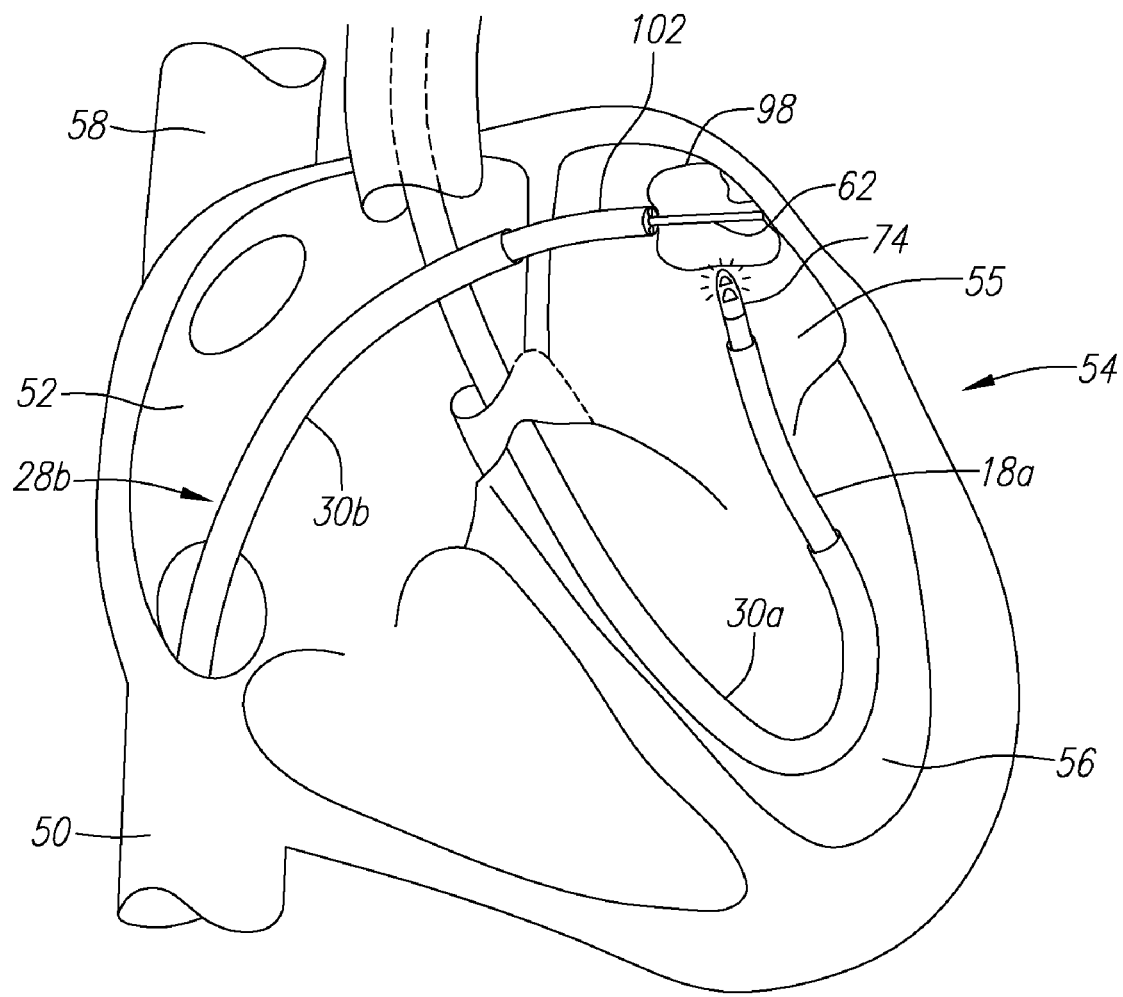
Figure 17A:
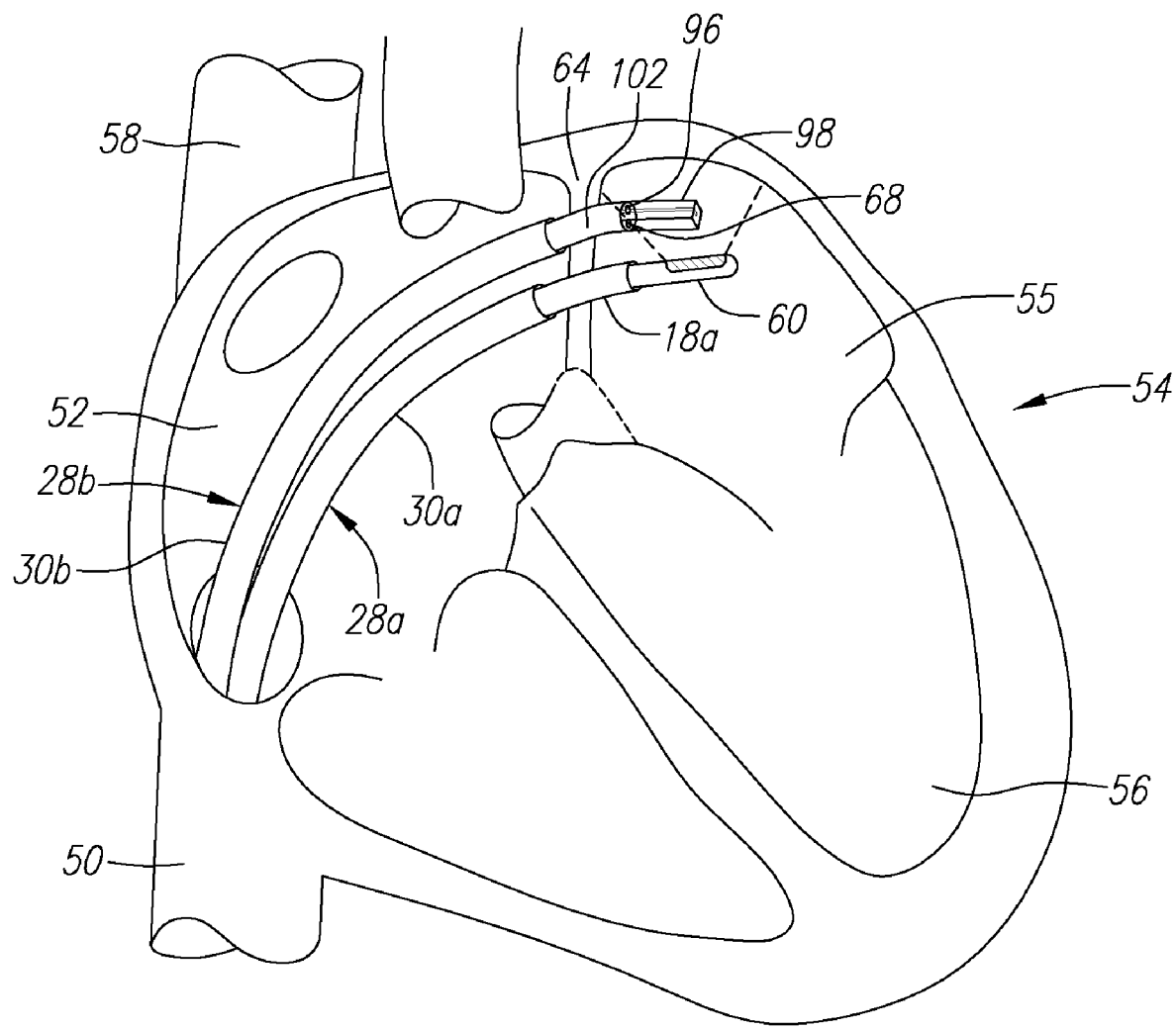
FIGS. 17A-17C illustrate another embodiment of an intracardiac system and procedure according to the present invention.
Figure 17B:
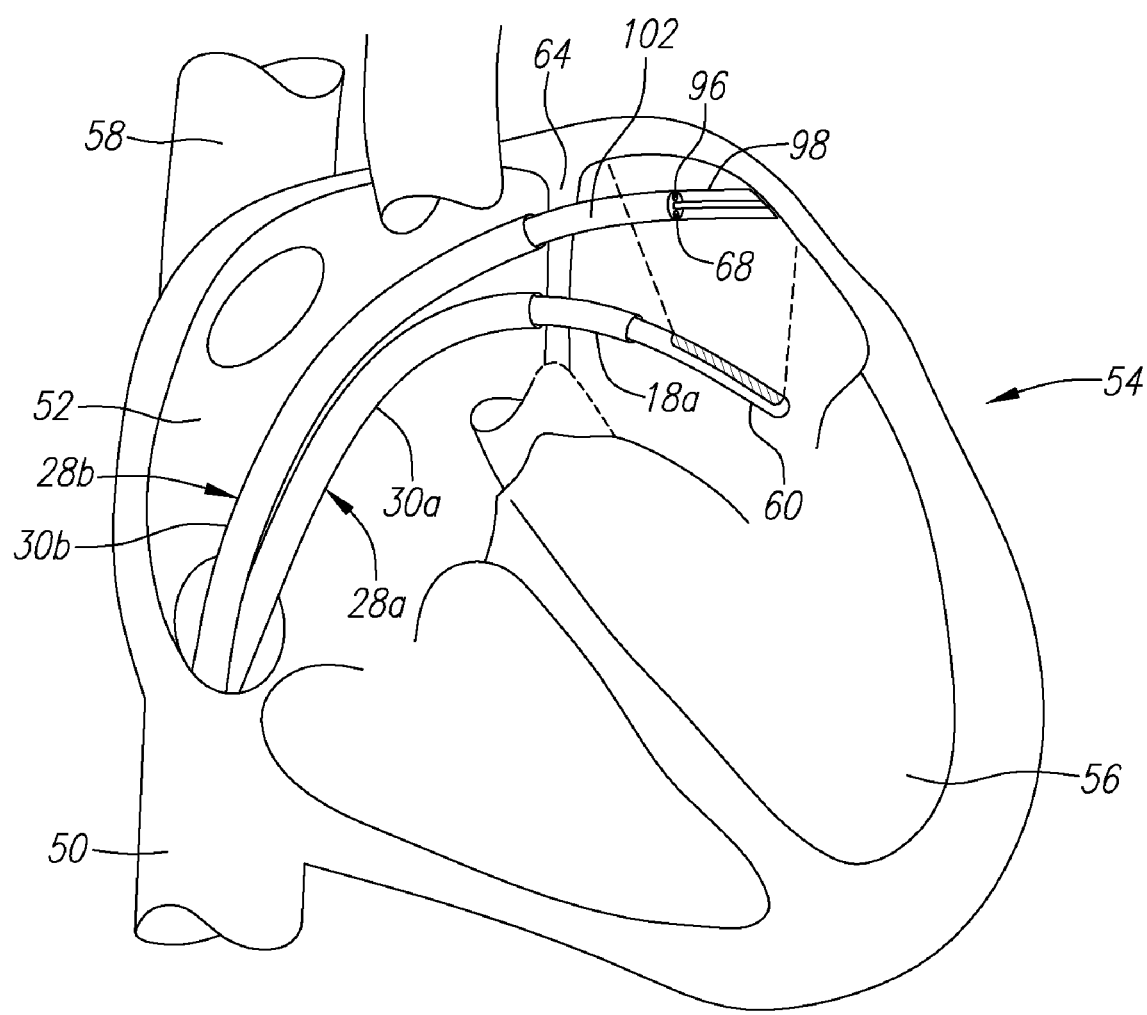
Figure 17C:
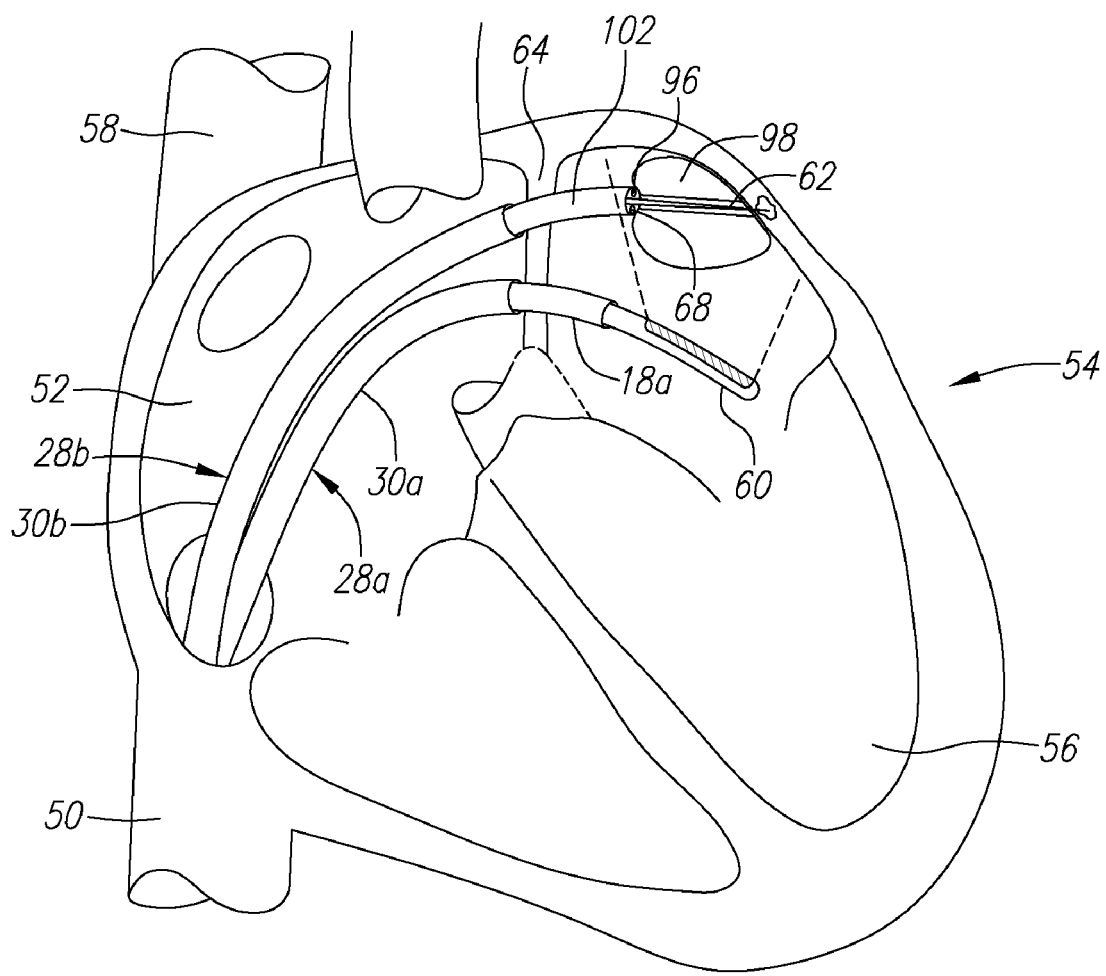

FIGS. 16A-16C depict another embodiment of an intracardiac system and procedure for positioning a cardioscopy catheter (102) with balloon (98) transseptally and performing a retrograde ablation. As shown in FIG. 16A, the first instrument assembly (28a) having an ablation catheter (74) is maneuvered retrograde into the left ventricle (56) and into the left atrium (55) as shown in FIG. 16B. The second instrument assembly (28b) having a cardioscopy catheter (102) is maneuvered through the inferior vena cava (50) into the right atrium 52 and then through the atrial septum (64) into the left atrium 55, as shown in FIG. 16B. The second instrument assembly (28b) is positioned proximate the ablation site and the balloon (98) is inflated such that it bears against the wall of the left atrium (55) thereby providing a clear field of view for the image capture device (68). Then, the ablation catheter (74) may be utilized to ablate tissue lesions in the left atrial (55) wall, while the image capture device may be used to monitor the ablation.

Referring to FIGS. 15A-15C, a transseptal injection therapy using ICE imaging is depicted. Like many of the embodiments described above, the first instrument assembly (28a) is provided with an ICE catheter (60). The second instrument assembly (28b) includes a cardioscopy catheter (102), as described above. The first and second instrument assemblies (28a and 28b) are positioned transseptally into the right atrium (55). The first instrument assembly (28a) is positioned to provide the ICE catheter (60) with a field of view of the injection site. The second instrument assembly (28b) is positioned proximate the injection site and the balloon (98) is inflated such that it bears against the wall of the left atrium (55) thereby providing a clear field of view for the image capture device (68). The needle (62) is then advanced into the injection site and fluid, such as a medicament, is injected into the tissue at the injection site.

Figure 18A:
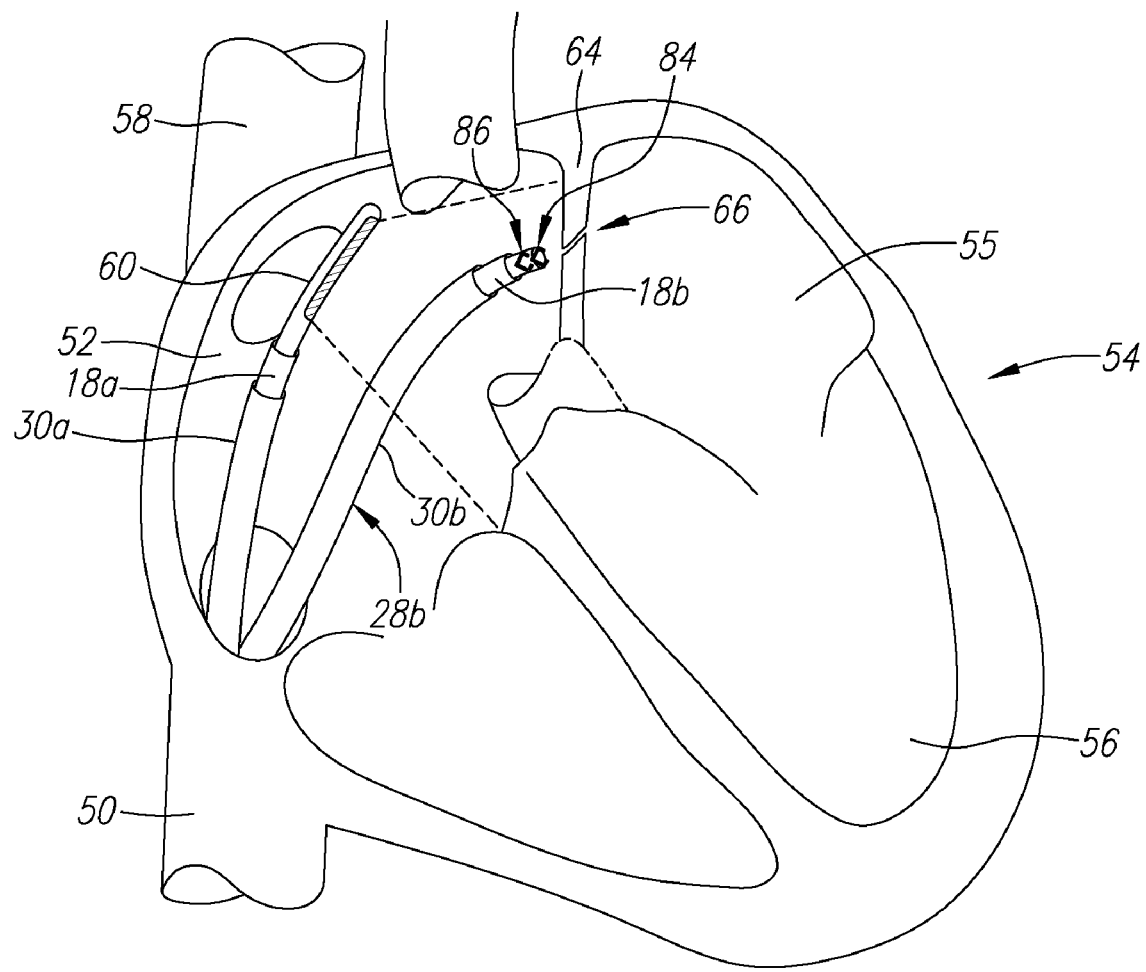
FIGS. 18A-18B illustrate another embodiment of an intracardiac system and procedure according to the present invention.
Figure 18B:
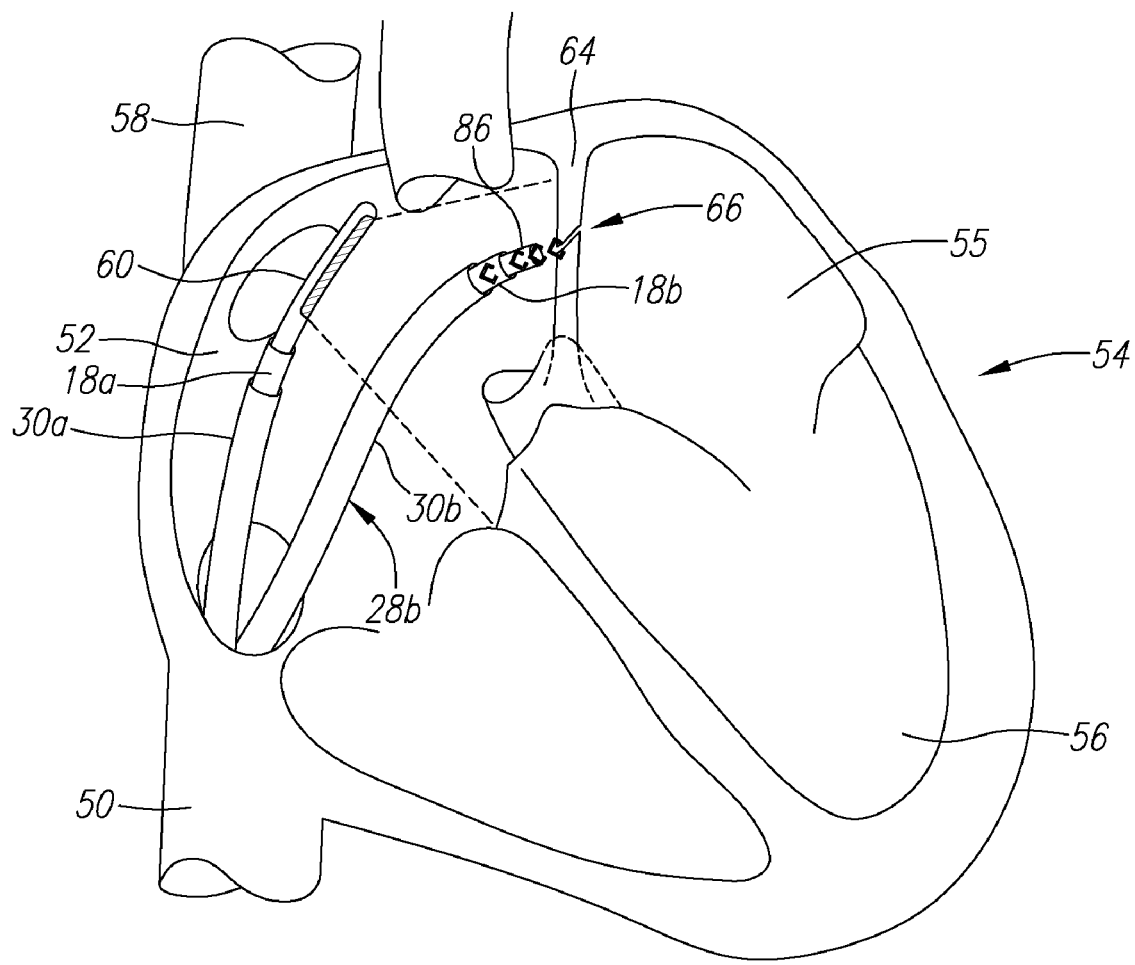

An intracardiac system and procedure for treating a PFO by deploying a clip (92) is depicted in FIGS. 18A-18B. The first instrument assembly (28a) is provided with an ICE catheter (60) while the second instrument assembly (28b) is provided with a clip applier (86). The first instrument assembly (28a) is positioned to give the ICE catheter (60) a field of view of the PFO (66). The second instrument assembly (28b) is maneuvered to position the clip applier (86) proximate the PFO (66) and the clip applier (86) deploys one or more clips (84) to close and heal the PFO (66), as shown in FIG. 18B.

Figure 19A:
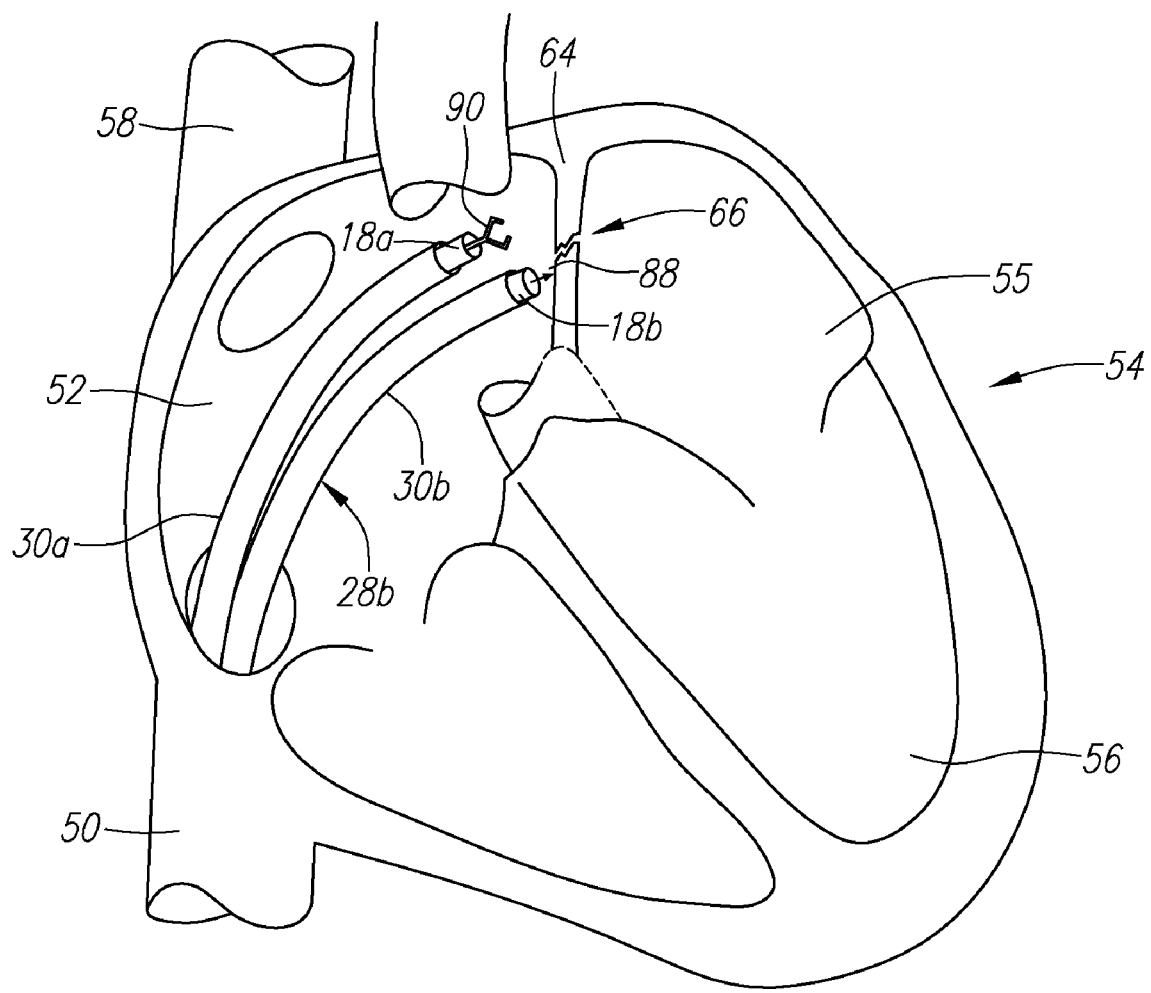
FIGS. 19A-19C illustrate another embodiment of an intracardiac system and procedure according to the present invention.
Figure 19B:
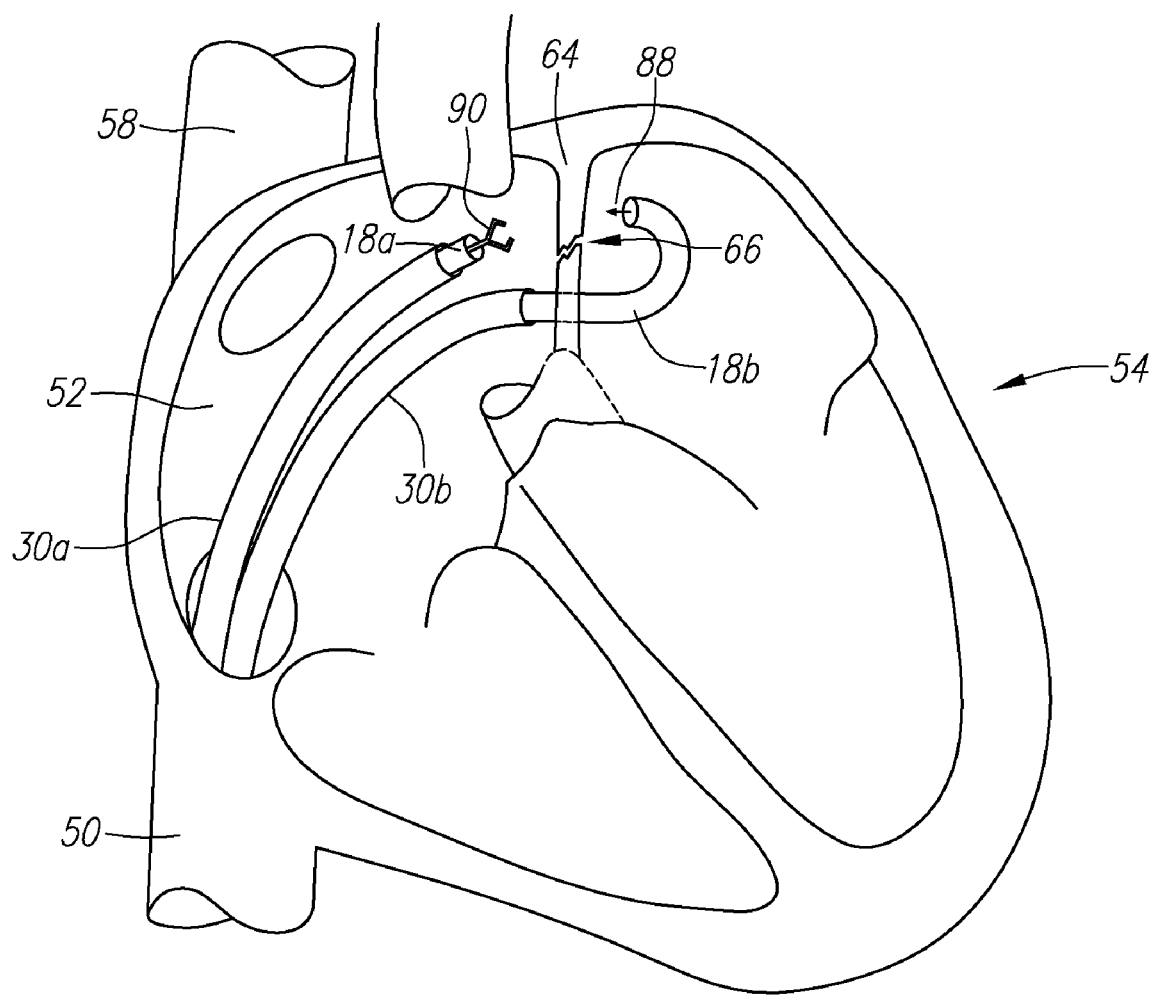
Figure 19C:
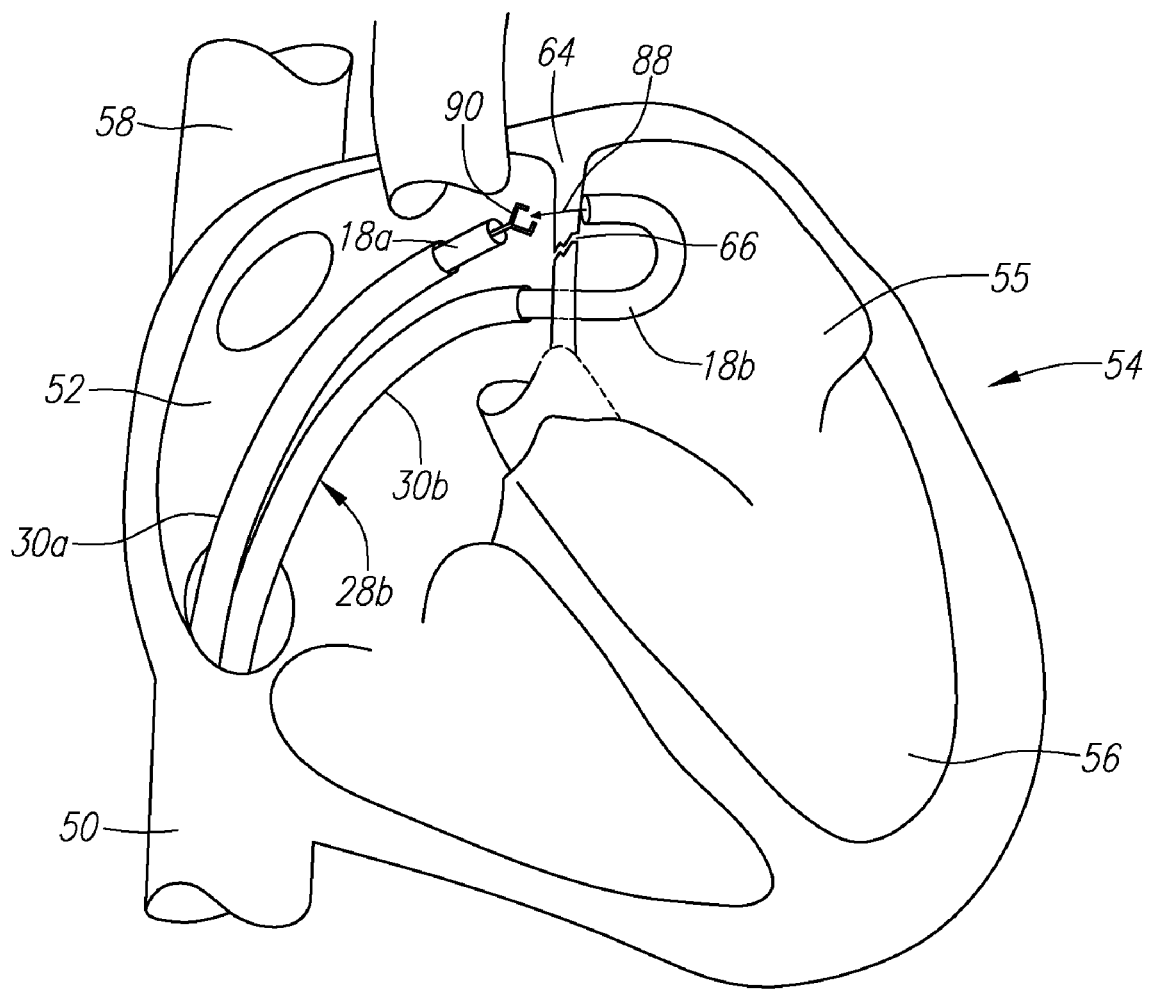

FIGS. 19A-19C depict another embodiment for treating a PFO, this time utilizing a needle and suture complex (88) and a grasping tool (90). The first instrument assembly (28a) includes a needle and suture complex (88), and is positioned transseptally, as shown in FIG. 19B. The second instrument assembly (28b) has a grasper (90) which is positioned proximate the atrial septum (64). The needle and suture complex (88) is advanced through the atrial septum (64) and the grasper (90) is used to grasp the needle of the complex (88) after it passes through the wall in order to apply tension to the suture complex (88) to close the PFO (66), as shown in FIG. 19C.

Figure 20A:
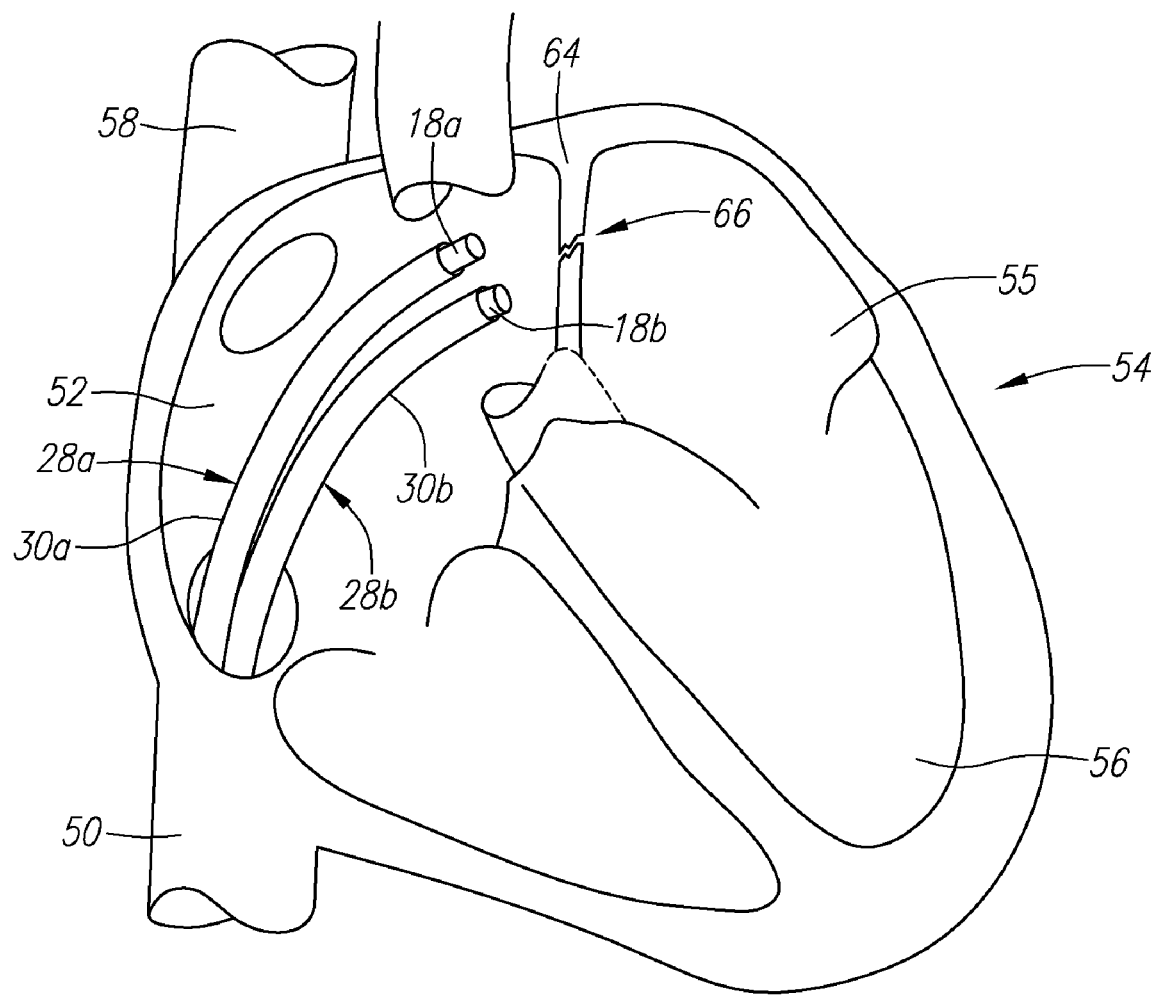
FIGS. 20A-20C illustrate another embodiment of an intracardiac system and procedure according to the present invention.
Figure 20B:
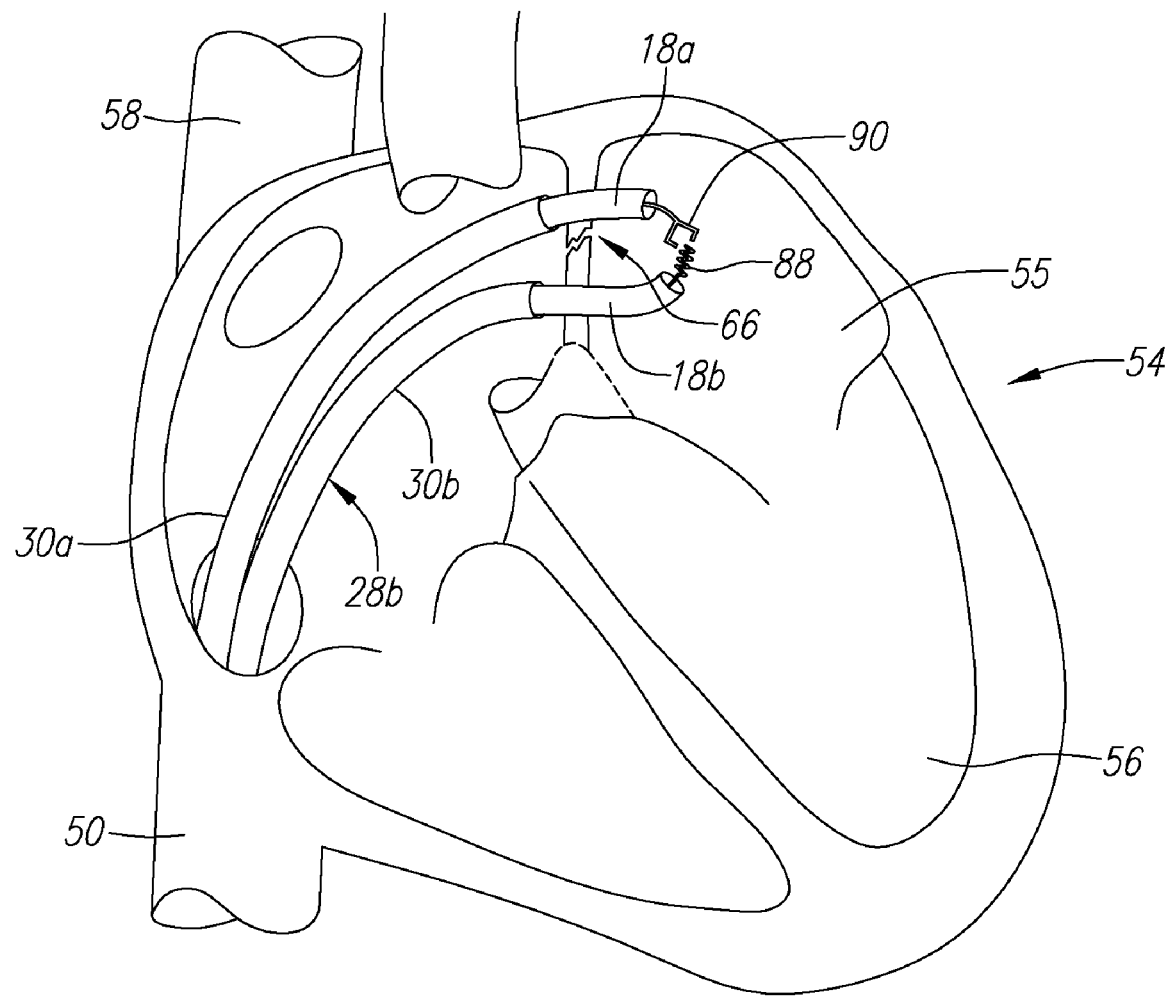
Figure 20C:
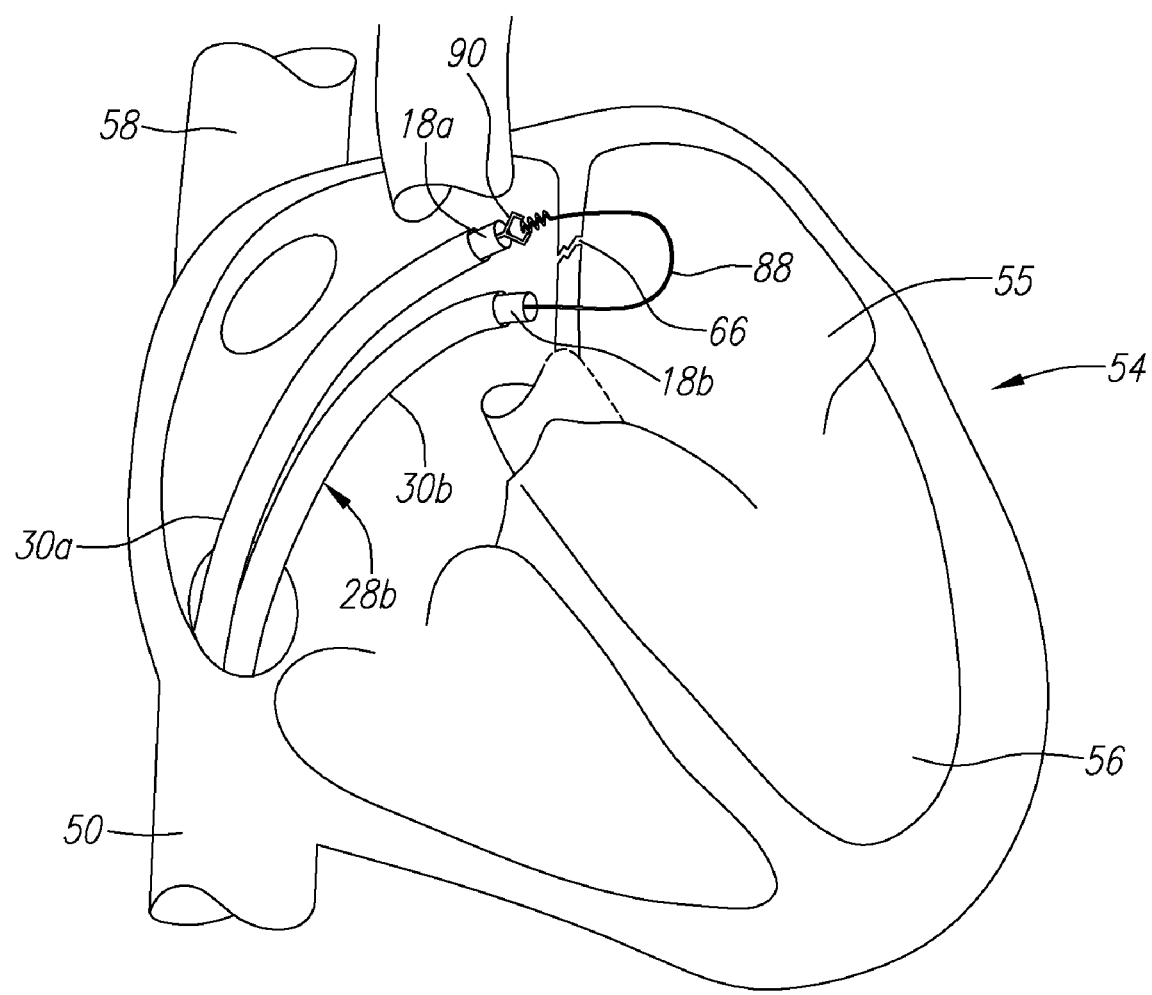

FIGS. 20A-20C depict an embodiment for treating a PFO (66) similar to FIGS. 19A-19C, except that both the first and second instrument assemblies (28a and 28b) are advanced transseptally. As shown in FIG. 20A, the first and second instrument assemblies (28a and 28b) are maneuvered into the left atrium (52) through the inferior vena cava (50) and proximate the atrial septum (64). Then, both instrument assemblies (28a and 28b) are advanced through the atrial septum (64) as shown in FIG. 20B. The needle and suture complex (88) is advanced toward the grasping tool (90) which grasps the needle. Then, both instrument assemblies (28a and 28b) are withdrawn out of the atrial septum (64) into the right atrium (52), as shown in FIG. 20C, thereby closing the PFO (66).

Figure 21A:
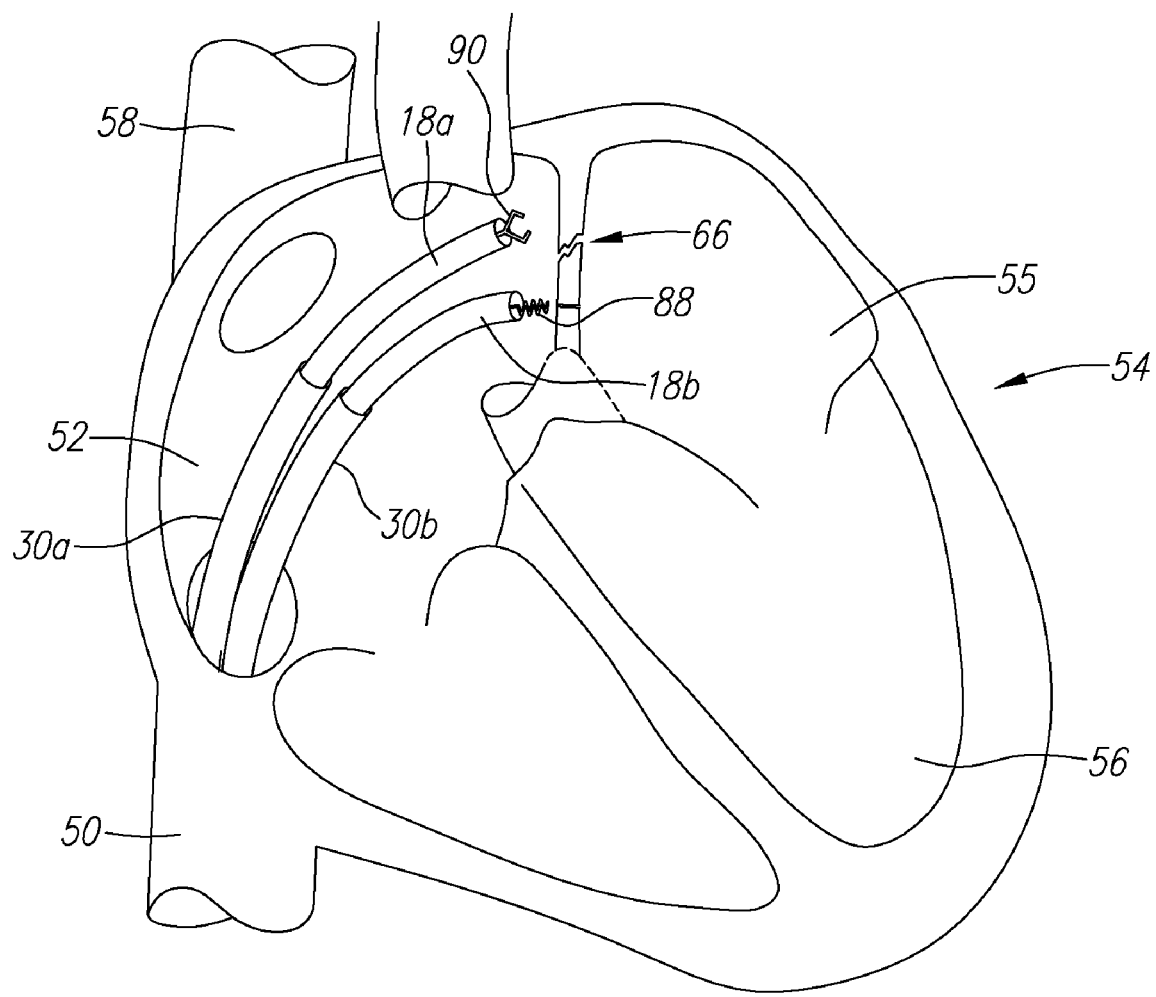
FIGS. 21A-21C illustrate another embodiment of an intracardiac system and procedure according to the present invention.
Figure 21B:
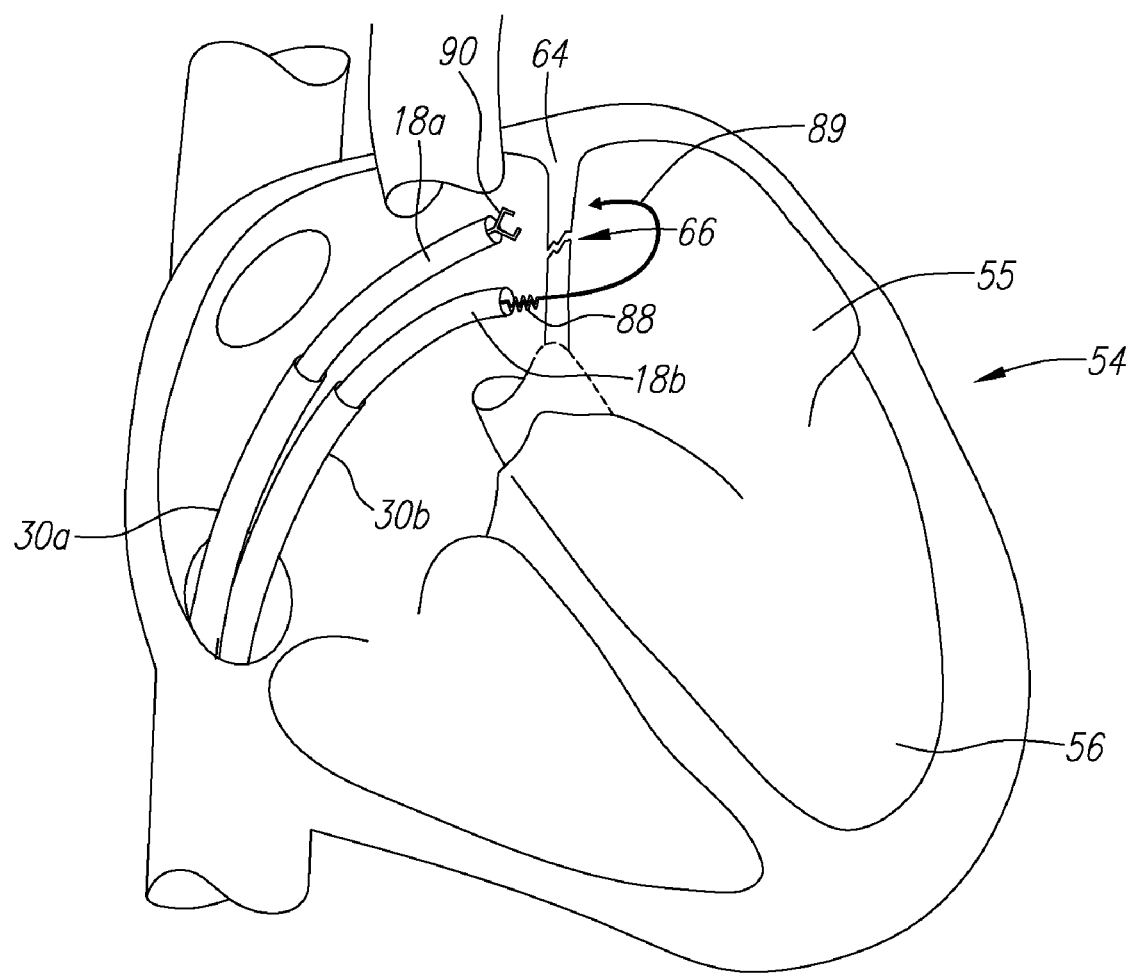
Figure 21C:
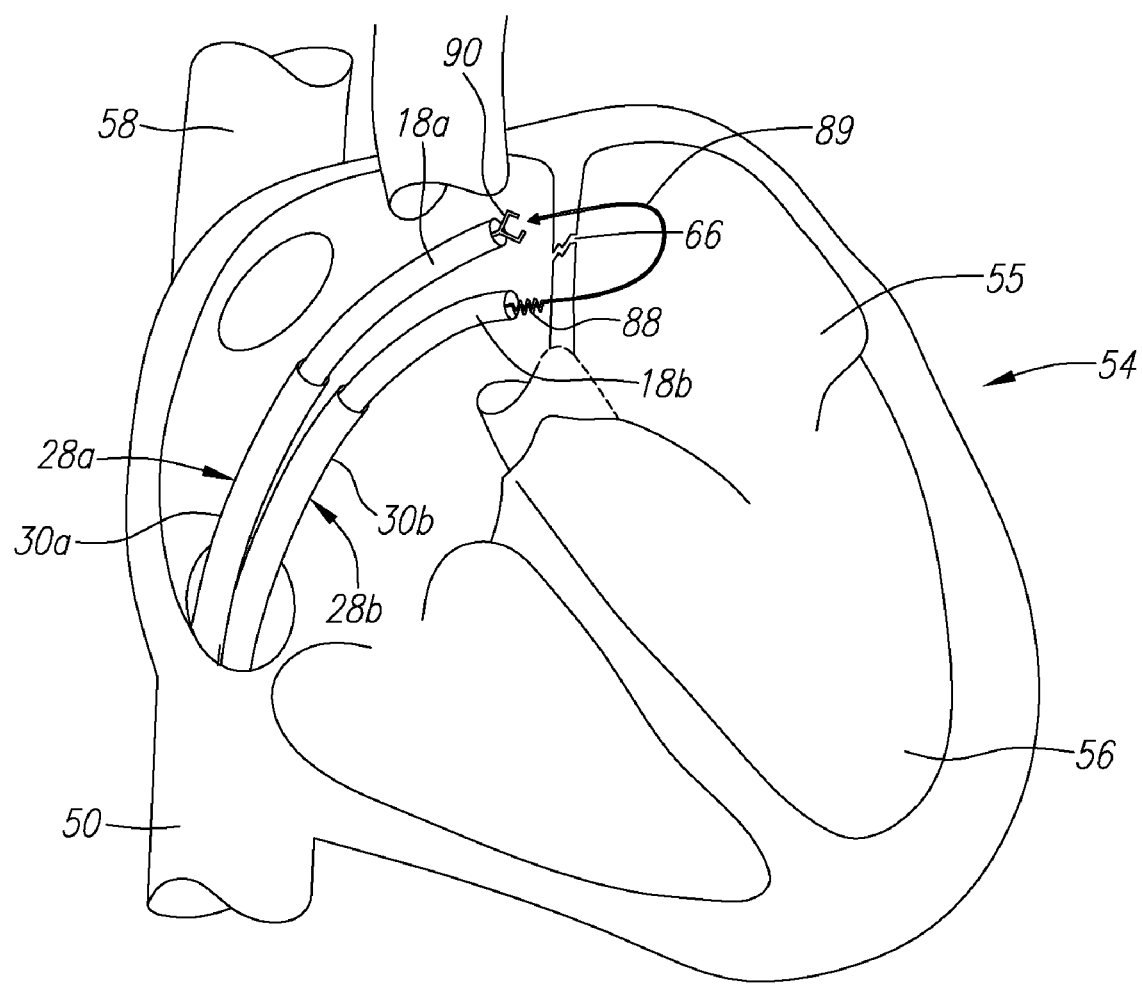

Referring to FIGS. 21A-21C, still another embodiment for treating a PFO (66) is depicted which is very similar to the embodiment shown in FIGS. 19A-19C, except that the first instrument assembly (28b) is not advanced through the atrial septum (64). Instead, only the needle and suture complex (88), having an arcuate needle (89), is advanced through the atrial septum (64) as shown in FIG. 21B. The arcuate needle (89) is then passed through the atrial septum (64) again back into the right atrium (52). The grasping tool (90) is then used to grasp the needle (89) to apply tension to the needle and suture complex (88) thereby closing the PFO (66).

Figure 22A:
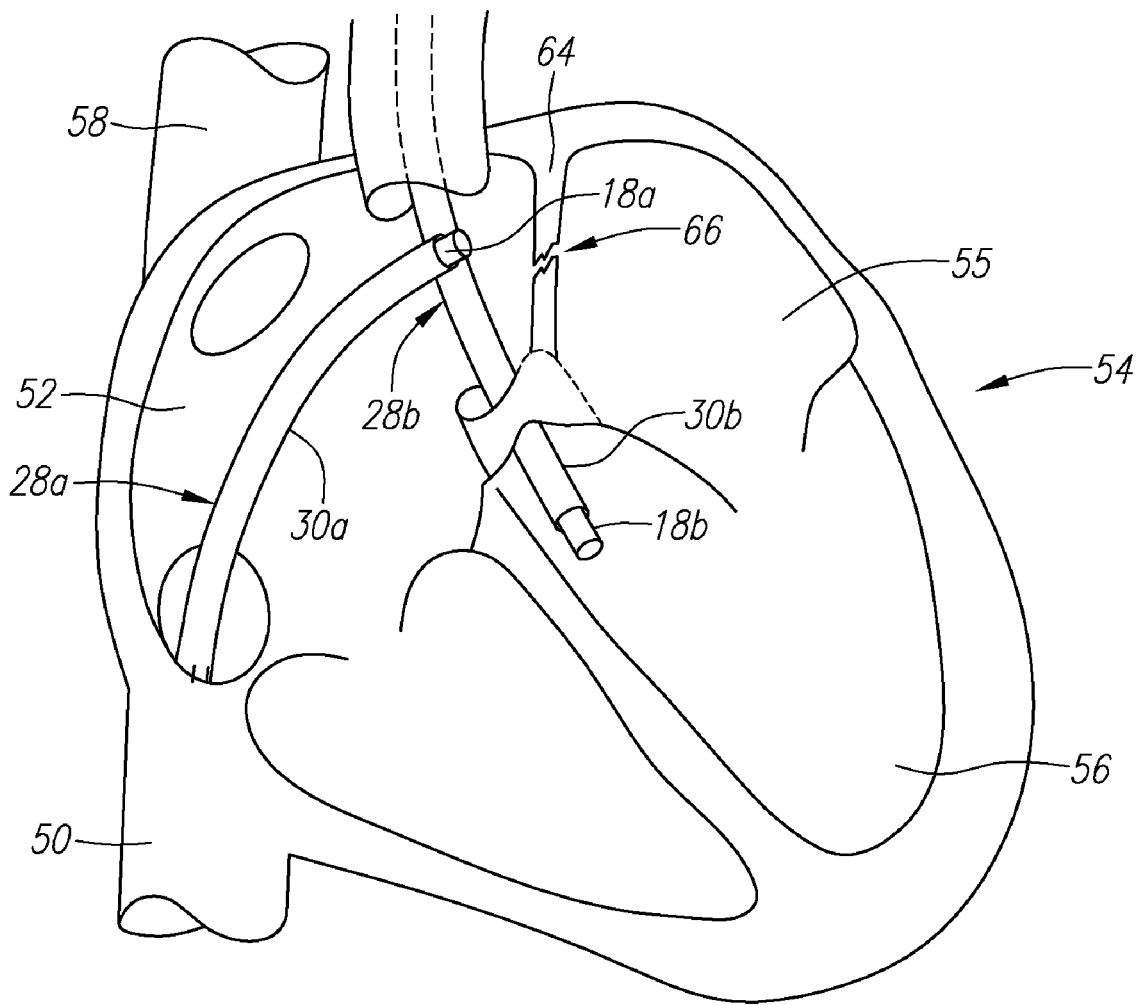
FIGS. 22A-22E illustrate another embodiment of an intracardiac system and procedure according to the present invention.
Figure 22B:
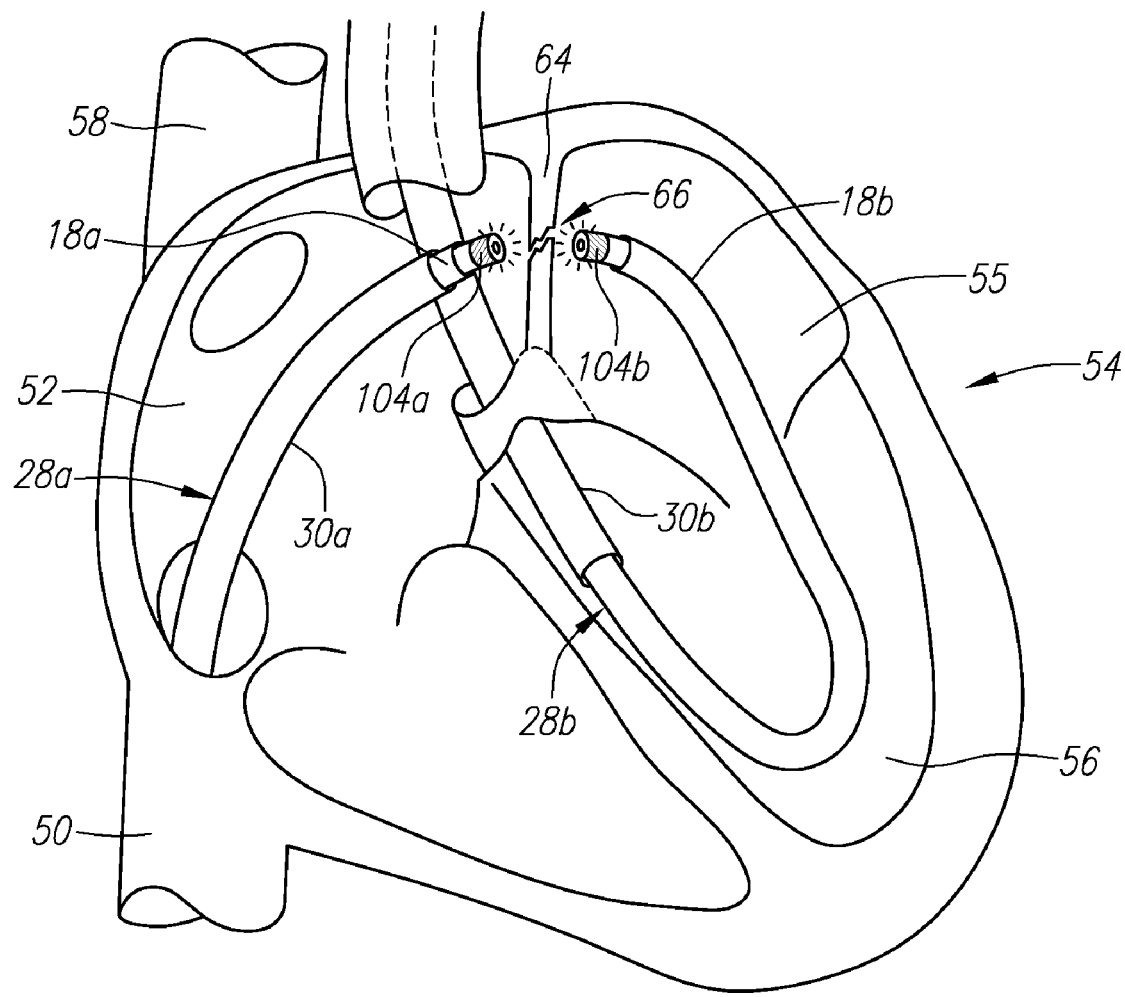
Figure 22C:
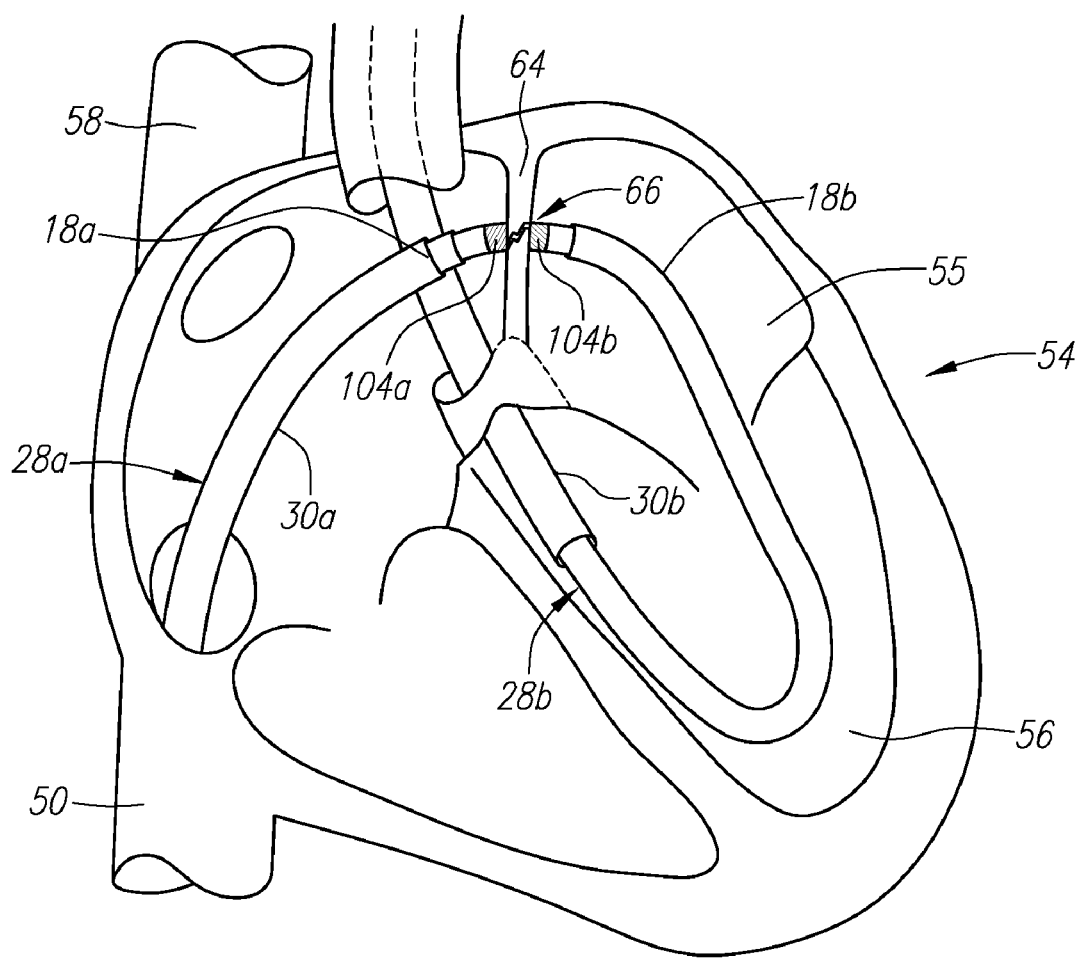
Figure 22D:
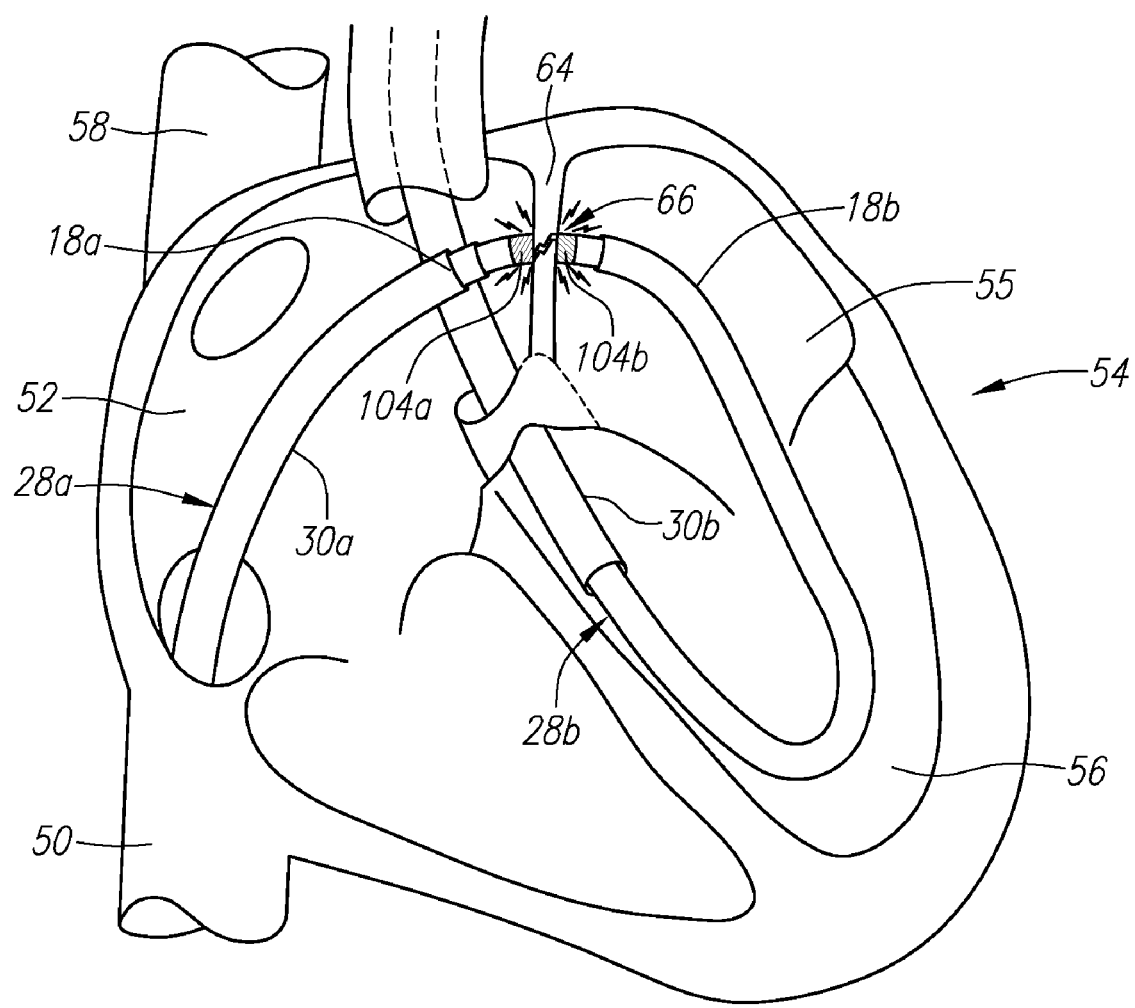
Figure 22E:
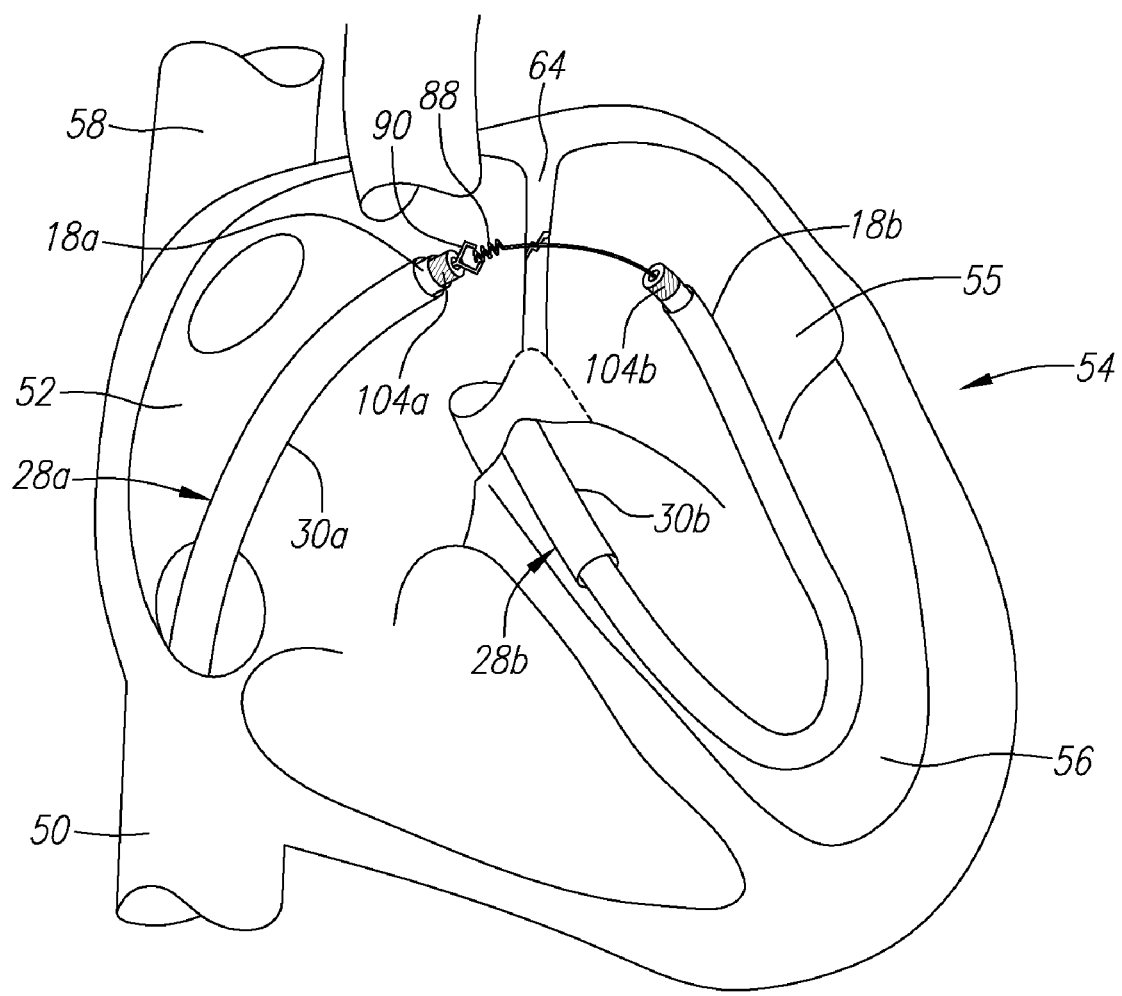

Turning to FIGS. 22A-21E, still another embodiment for treating a PFO (66) is depicted which utilizes magnetic clips and a needle and suture complex. As shown in FIGS. 22A and 22B, the first instrument assembly (28a) has a magnetic clip (104a) and is maneuvered into the right atrium (52) proximate the atrial septum (64). The second instrument assembly (28b) also has a magnetic clip (104b), and it is maneuvered retrograde into the left atrium (55) proximate the atrial septum (64) opposite the magnetic clip (104a). As shown in FIG. 22C, the two magnetic clips (104a and 104b) bear against opposite sides of the atrial septum (64) which closes the PFO (66). With the PFO (66) closed by the magnetic clips (104a and 104b), a needle and suture complex (88) is advanced from the second instrument assembly (28b) through the atrial septum (64) at the site of the PFO (66), as depicted in FIG. 22D. The grasping tool (90) on the first instrument assembly (28a) grasps the needle and suture complex (88) and pulls it tight. The magnetic clips (104a and 104b) are then withdrawn from each other, as shown in FIG. 22E, while the suture holds the PFO closed.

While multiple embodiments and variations of the many aspects of the invention have been disclosed and described herein, such disclosure is provided for purposes of illustration only. Many combinations and permutations of the disclosed system are useful in minimally invasive surgery, and the system is configured to be flexible. For example, depending upon the medical application, it may be desirable to have a guide instrument with less than four control elements, combined with a sheath instrument, or perhaps combined with a prebent, unsteerable sheath, or perhaps with no sheath at all. The instrument driver may be tailored to match the instrument configuration, with less motors and gearboxes for less control elements, or variation in the configuration for actuating a given control element interface assembly, and associated variation in the tensioning mechanism and number of control element pulleys associated with the pertinent control element interface assembly (one pulley and one cable per control element interface assembly, two pulleys and two cables per control element interface assembly, slotted, split carriage, and winged split carriage embodiments, various tensioning embodiments, etc).

What we claim is:

1. A robotic instrument system, comprising:
   one or more controllers;
   a first support structure;
   a first instrument drive assembly operatively coupled to at least one of the one or more controllers, and detachably coupled to said first support structure, said first instrument drive assembly comprising one or more motors configured to operate a first instrument assembly;
   a first instrument assembly detachably coupled to said first instrument drive assembly, said first instrument assembly comprising a first elongate, flexible guide instrument configured to be steered within a lumen of a patient's body;
   a second support structure;
   a second instrument drive assembly operatively coupled to at least one of the one or more controllers, and detachably coupled to said second support structure, said second instrument drive assembly comprising one or more motors configured to operate a second instrument assembly; and a second instrument assembly detachably coupled to said second instrument drive assembly, said second instrument assembly comprising a second elongate, flexible guide instrument configured to be steered within a lumen of the patient's body, wherein the one or more controllers are configured to selectively actuate respective motors in the first and second instrument drive assemblies to thereby selectively move respective distal end portions of the respective first and second elongate, flexible guide instruments in response to control signals generated, at least in part, by one or more input devices coupled to the one or more controllers, and wherein said first instrument assembly further comprises a first elongate sheath instrument, and said second instrument assembly further comprises a second elongate sheath instrument, the first and second elongate, flexible guide instruments being carried in a coaxial configuration in the respective first and second elongate sheath instruments, and said first and second instrument drive assemblies comprise respective drive elements configured to independently operate the respective first and second elongate sheath instruments and first and second elongate, flexible guide instruments, wherein each of the first and second elongate, flexible guide instruments is configured to move relative to each of the first and second elongate sheath instruments, respectively.

2. The system of claim 1, wherein the one or more controllers comprise a single controller operatively coupled to the first and second instrument drive assemblies.

3. The system of claim 1, wherein the one or more controllers comprise a first controller operatively coupled to the first instrument drive assembly, and second controller in communication with the first controller and operatively coupled to the second instrument drive assembly.

4. The system of claim 1, wherein said first support structure and said second support structure are configured to be respectively coupled to opposing sides of an operating table.

5. The system of claim 1, wherein said first support structure and said second support structure are configured to be respectively coupled to a same side of an operating table.

6. The system of claim 1, wherein said first and second support structures comprise respective articulating arms.

7. A method for performing a minimally invasive intracardiac surgical procedure on a patient's heart, the method comprising:
providing a robotic instrument system comprising:
one or more controllers;
a first instrument drive assembly operatively coupled to at least one of the one or more controllers and comprising one or more motors configured to operate a first instrument assembly;
a first instrument assembly detachably coupled to said first instrument drive assembly, said first instrument assembly comprising a first elongate, flexible guide instrument configured to be inserted into a patient's body, the first elongate, flexible guide instrument having a distal end;
a second instrument drive assembly operatively coupled to at least one of the one or more controllers and comprising one or more motors configured to operate a second instrument assembly; and
a second instrument assembly detachably coupled to said second instrument drive assembly, said second instrument assembly comprising a second elongate, flexible guide instrument configured to be inserted into a patient's body, the second elongate, flexible guide instrument having a distal end;
maneuvering said distal end of said first elongate, flexible guide instrument into the patient's heart by actuating said first instrument drive assembly; and
maneuvering said distal end of said second elongate, flexible guide instrument into the patient's heart by actuating said second instrument drive assembly.

8. The method of claim 7, wherein said distal end of said first elongate, flexible guide instrument is maneuvered into the patient's heart through the inferior vena cava and into the right atrium, and said distal end of said second elongate, flexible guide instrument is maneuvered into the patient's heart through the inferior vena cava and into the right atrium.

9. The method of claim 7, wherein said distal end of said first elongate, flexible guide instrument is maneuvered into the patient's heart through the inferior vena cava and into the right atrium, and said distal end of said second elongate, flexible guide instrument is maneuvered into the patient's heart through the superior vena cava and into the right atrium.

10. The method of claim 7, wherein an imaging transducer is provided on said distal end of said first elongate, flexible guide instrument and a cutting instrument is provided on said distal end of said second elongate, flexible guide instrument.

11. The method of claim 7, further comprising the step of performing a patent foramen ovale (PFO) procedure using said first and second elongate, flexible guide instruments.

12. The method of claim 7, further comprising the step of ablating intracardiac heart tissue.

13. The method of claim 7, further comprising the step of treating a left atrial appendage using said first and second elongate, flexible guide instruments.

14. The method of claim 7, further comprising the step of performing a transseptal mitral annulus tuning procedure using said first and second elongate, flexible guide instruments.

* * * * *